US008734367B2

(12) United States Patent
Barlow et al.

(10) Patent No.: US 8,734,367 B2
(45) Date of Patent: *May 27, 2014

(54) METHOD AND APPARATUS FOR MEASURING NON-NUTRITIVE SUCK PATTERN STABILITY

(75) Inventors: Steven M. Barlow, Lawrence, KS (US); Jingyan Wang, Lawrence, KS (US)

(73) Assignee: University of Kansas, Lawrence, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/555,976

(22) Filed: Jul. 23, 2012

(65) Prior Publication Data

US 2013/0023796 A1 Jan. 24, 2013

Related U.S. Application Data

(62) Division of application No. 12/390,142, filed on Feb. 20, 2009, now Pat. No. 8,226,579.

(60) Provisional application No. 61/030,484, filed on Feb. 21, 2008, provisional application No. 61/036,304, filed on Mar. 13, 2008.

(51) Int. Cl.
*A61B 5/103* (2006.01)
*A61B 5/117* (2006.01)

(52) U.S. Cl.
USPC .......................................................... 600/587

(58) Field of Classification Search
USPC .................. 600/587, 590; 702/179
See application file for complete search history.

(56) References Cited

U.S. PATENT DOCUMENTS

| 4,232,687 A | 11/1980 | Anderson et al. |
| 5,830,235 A | 11/1998 | Standley et al. |
| 6,033,367 A | 3/2000 | Goldfield |
| 8,226,579 B2 | 7/2012 | Barlow et al. |
| 2006/0074354 A1 | 4/2006 | Barlow et al. |
| 2009/0156967 A1 | 6/2009 | Cohen |
| 2009/0222214 A1 | 9/2009 | Barlow et al. |

FOREIGN PATENT DOCUMENTS

| CN | 101080195 A | 11/2007 |
| WO | WO-2006026623 A2 | 3/2006 |

OTHER PUBLICATIONS

"Chinese Application Serial No. 200910008046.7, Office Action mailed Jan. 29, 2013", (w/ English Summary), 4 pgs.
"Chinese Application Serial No. 200910008046.7, Office Action mailed Jul. 31, 2012", (w/ English Translation), 10 pgs.
"Chinese Application Serial No. 200910008046.7, Response filed Mar. 21, 2013 to Office Action mailed Jan. 29, 2013", (w/ English claims), 5 pgs.

(Continued)

*Primary Examiner* — Rene Towa
(74) *Attorney, Agent, or Firm* — Schwegman Lundberg & Woessner, P.A.

(57) ABSTRACT

Method and apparatus are provided for generating an index associated with non-nutritive suck pattern stability. An example apparatus can include an STI generator configured to generate a plurality of non-nutritive suck (NNS) pressure samples using a non-nutritive pacifier and a pressure transducer, and to sum a plurality of standard deviations based on the plurality of NNS pressure samples to provide a spatiotemporal index (STI) of non-nutritive suck pattern stability, wherein the STI is configured to provide a composite indication of variability of amplitude, and duration of a plurality of portions of the NNS pressure samples.

14 Claims, 23 Drawing Sheets

(56) References Cited

OTHER PUBLICATIONS

"Chinese Application Serial No. 200910008046.7, Response filed Dec. 14. 2012 to Office Action mailed Jul. 31, 2012", (w/ English Claims), 5 pgs.

"European Application Serial No. 09250464.6, Response filed Oct. 25, 2012 to Extended Search Report mailed Mar. 22, 2012", 8 pgs.

"U.S. Appl. No. 12/390,142, Response filed Jan. 11, 2012 to Non Final Office Action mailed Jul. 11, 2011", 11 pgs.

"U.S. Appl. No. 12/390,142, Response filed Mar. 27, 2012 to Final Office Action mailed Jan. 27, 2012", 10 pgs.

"U.S. Appl. No. 12/390,142, Response filed May 3, 2012 to Final Office Action mailed Jan. 27, 2012 and Advisory Action mailed Apr. 11, 2012", 13 pgs.

"U.S. Appl. No. 12/390,142, Advisory Action mailed Apr. 11, 2012", 6 pgs.

"U.S. Appl. No. 12/390,142, Final Office Action mailed Jan. 27, 2012", 11 pgs.

"U.S. Appl. No. 12/390,142, Non Final Office Action mailed Jul. 11, 2011", 11 pgs.

"U.S. Appl. No. 12/390,142, Notice of Allowance mailed May 14, 2012", 8 pgs.

"U.S. Appl. No. 12/390,142, Preliminary Amendment filed May 8, 2009", 6 pgs.

"U.S. Appl. No. 12/390,142, Preliminary Amendment filed Jun. 8, 2011", 3 pgs.

"U.S. Appl. No. 12/390,142, Response filed Jun. 6, 2011 to Restriction Requirement mailed May 4, 2011", 6 pgs.

"U.S. Appl. No. 12/390,142, Restriction Requirement mailed May 4, 2011", 5 pgs.

"U.S. Appl. No. 200910008046.7, Office Action mailed Jul. 17, 2009", 1 pg.

"Application Serial No. 200910008046.7, Office Action dated Apr. 24, 2009".

"Application Serial No. 200910008046.7, Office Action Mailed Aug. 13, 2009", 2 pgs.

"Chinese Applicaiton Serial No. 200910008046.7, Response filed Apr. 28, 2012 to Office Action mailed Dec. 13, 2011", 4 pgs.

"Chinese Application Serial No. 200910008046.7, Office Action mailed Dec. 13, 2011", 5 pgs.

"European Application Serial No. 09250464.6, Office Action mailed Mar. 22, 2012", 11 pgs.

Barlow, S M, et al., "Synthetic orocutaneous stimulation entrains preterm infants with feeding difficulties to suck", Journal of Perinatology, vol. 28, No. 8, (Aug. 1, 2008), 541-548.

Barlow, S. M., et al., "Mechanically Evoked Perioral Reflexes in Infants", Brain Research, 599(1), (1992), 158-160.

Estep, Meredith, et al., "Non-nutritive suck parameters in preterm infants with RDS", Journal of Neonatal Nursing, vol. 14, No. 1, (28-34), Jan. 30, 2008.

Finan, D. S, et al., "The Actifier: A Device for Neurophysiological Studies of Orofacial Control in Human Infants", Journal of Speech and Hearing Research, vol. 39, (Aug. 1, 1996), 833-838.

Lau, C., "Oral Feeding in the Preterm Infant", NeoReviews, 7 (1), (Jan. 2006), e19-e27.

Poore, M, et al., "Respiratory treatment history predicts suck pattern stability in preterm infants", Journal of Neonatal Nursing, vol. 14, No. 6, (Dec. 1, 2008), 185-192.

Popescue, E A, et al., "Non-nutritive sucking recorded in utero via fetal magnetograph", Physiological Measurement, vol. 29, No. 1, (Jan. 1, 2008), 127-139.

Stumm, Susan, et al., "Respiratory distress syndrome degrades the fine structure of the non-nutritive suck in preterm infants", Journal of Neonatal Nursing, vol. 14, No. 1, (Dec. 26, 2007), 1355-1841.

"Chinese Application Serial No. 200910008046.7, Response filed Jul. 1, 2009 to Office Action mailed Apr. 24, 2009", (w/ Amended Drawings), 10 pgs.

"Chinese Application Serial No. 200910008046.7, Response filed Sep. 16, 2009 to Office Action mailed Jul. 17, 2009", (w/ Amended Drawings), 4 pgs.

"European Application Serial No. 09250464.6, Communication pursuant to Rules 70(2) and 70a(2) EPC mailed May 2, 2012", 2 pgs.

"European Application Serial No. 09250464.6, Office Action mailed Jul. 2, 2013", 6 pgs.

"European Application Serial No. 09250464.6, Response filed Oct. 25, 2012 to Communication mailed May 2, 2012", 8 pgs.

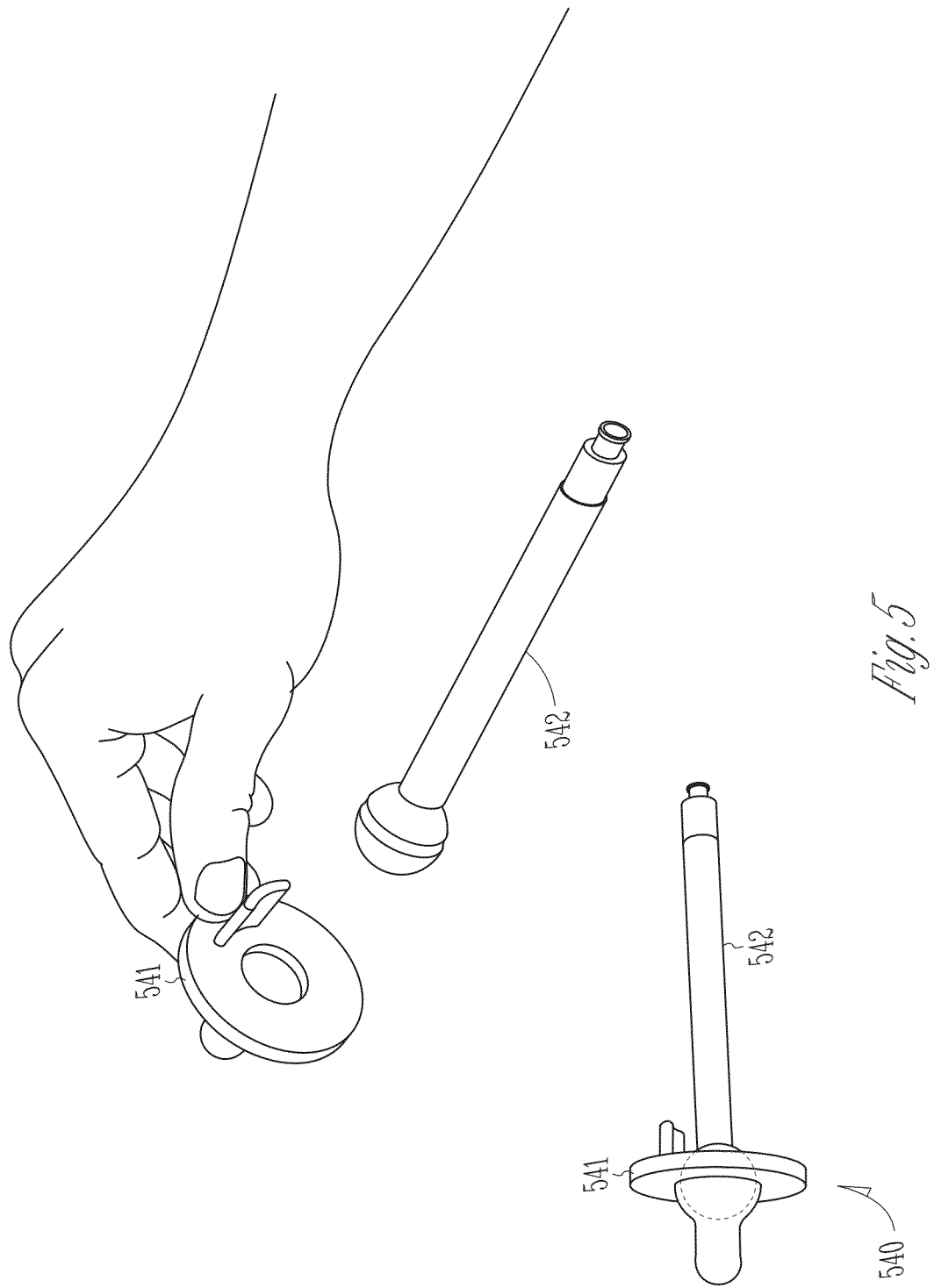

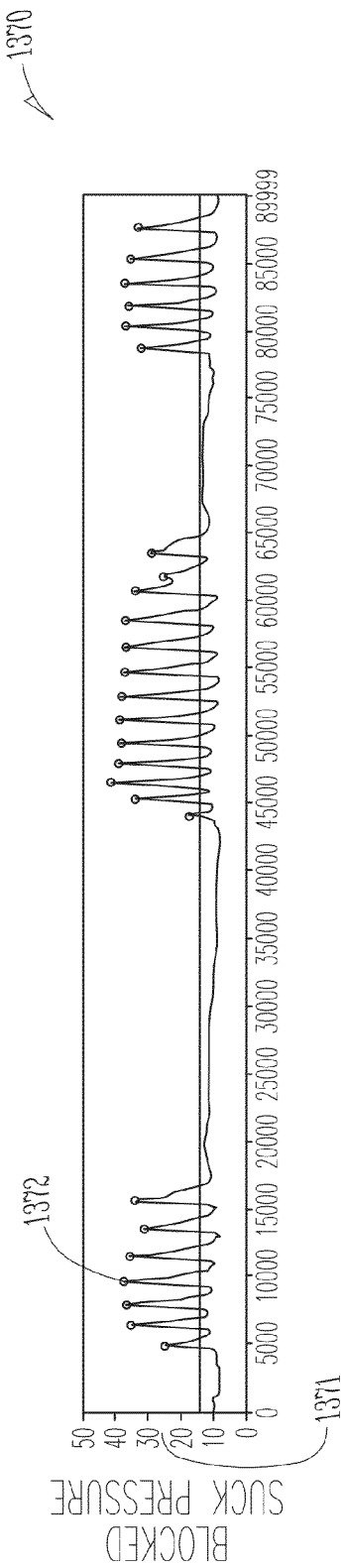
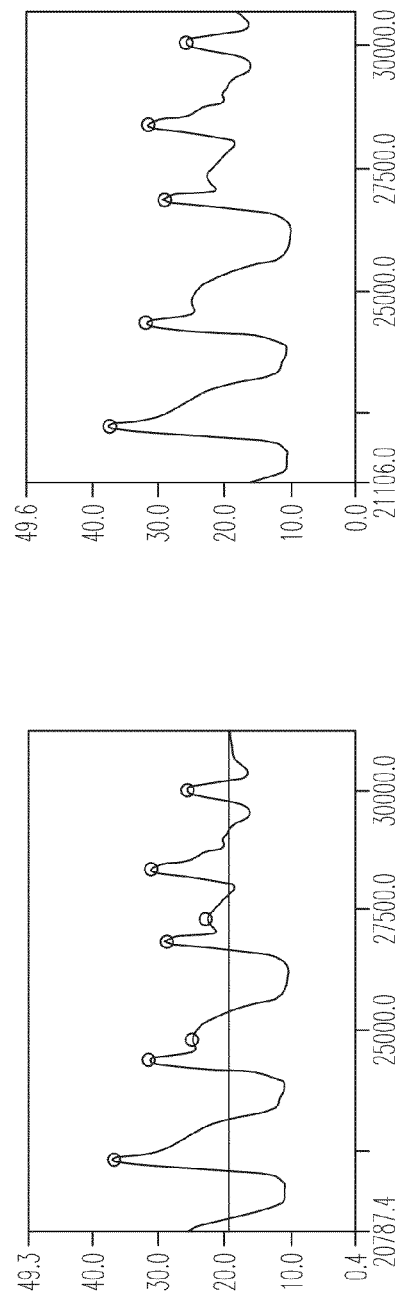
Fig. 13
Fig. 14A
Fig. 14B

METHOD AND APPARATUS FOR MEASURING NON-NUTRITIVE SUCK PATTERN STABILITY

RELATED APPLICATIONS

This application is a divisional of and claims the benefit of priority under 35 U.S.C. §120 to U.S. patent application Ser. No. 12/390,142, filed on Feb. 20, 2009, and claims the benefit under 35 U.S.C. 119(e) of U.S. Provisional Patent Application Ser. No. 61/030,484 filed Feb. 21, 2008 and U.S. Provisional Patent Application Ser. No. 61/036,304 filed Mar. 13, 2008, which are incorporated herein by reference in their entirety.

STATEMENT REGARDING FEDERALLY SPONSORED RESEARCH OR DEVELOPMENT

This invention was made with government support under award number NIH R01 DC03311-06 from the National Institutes for Health. The government has certain rights in this invention.

FIELD OF TECHNOLOGY

This document relates to improving non-nutritive suck skill and more particularly to generating a spatiotemporal index to monitor non-nutritive suck pattern stability.

BACKGROUND

Sucking is a precocial motor behavior in humans. However, premature infants often demonstrate oromotor dyscoordination and are unable to suck or feed orally. This inability to feed can delay discharge from neonatal intensive care units and hinder development of coordinated oromotor behavior.

Infants' readiness to feed is often evaluated by their display of non-nutritive sucking (NNS). Suck is manifest in-utero between 15 and 18 weeks gestation age (GA). NNS typically begins between 28 and 33 weeks GA and is remarkably stable by 34 weeks. Non-nutritive suck normally comprises a series of suck activity bursts separated by pauses. Each burst consists of 6 to 12 suck cycles that occur at approximately 2 Hz and are separated by pauses for respiration. The mammalian NNS is primarily controlled by the suck central pattern generator (sCPG), which includes bilateral internuncial circuits within the brainstem reticular formation. The minimal circuitry for ororhythmic activity resides between the trigeminal motor nucleus and the facial nucleus in the brainstem.

Some patients, including, but not limited to pre-mature infants, often demonstrate oromotor discoordination and are unable to suck and feed orally. Oromotor discoordination represents challenge to neonatal care unit survivors and the survivor caretakers. Potential causes of oromotor discoordination or impaired suck development are numerous and include, but are not limited to, neurological insult to the developing brain, feeding intolerance and interventions that interfere with ororhythmic pattern formation. For example, lengthy oxygen supplementation procedures can interfere with ororhythmic pattern formation.

In current practice, infant NNS evaluation is still quite subjective. Typically, NNS is evaluated by placing a gloved finger in the infant's mouth to observe the rhythmicity, strength, cycle frequency, and burst duration of NNS. Clinical observations can then be characterized with validated scales, such as the NOMAS®, which are designed to assess sucking patterns in preterm infants and monitor changes over time, or the Early Feeding Skills (EFS) Assessment, which is a checklist of suck-swallow coordination and physiological stability.

An objective and quantitative measure of oromotor ability would greatly benefit neonatal intensive care diagnostics and treatment.

SUMMARY

This application addresses the foregoing needs in the art and other needs not discussed herein. One embodiment of the present subject relates to a method for generating a index of non-nutritive suck development. The method includes measuring a plurality of non-nutritive suck (NNS) pressure samples, generating a plurality of correlation values using the NNS pressure samples, and generating a measure of non-nutritive suck development using the plurality of correlation values.

In various embodiments, an apparatus is provided comprising a processor and memory coupled to the processor. The memory including computer executable instructions configured to receive non-nutritive suck data, normalize a plurality of identified non-nutritive suck events within the non-nutritive suck data, and generate a correlation factor indicative of non-nutritive suck stability using the plurality of normalized non-nutritive suck events.

This Summary is an overview of some of the teachings of the present application and is not intended to be an exclusive or exhaustive treatment of the present subject matter. Further details about the present subject matter are found in the detailed description and the appended claims. The scope of the present invention is defined by the appended claims and their legal equivalents.

BRIEF DESCRIPTION OF DRAWINGS

FIG. 5 shows a pacifier apparatus 540 according to one embodiment of the present subject matter for use in collecting data samples for generating NNS-STI.

FIG. 13 shows a "Block Suck Pressure" plot according to one embodiment of the present subject matter.

FIGS. 14A and 14B illustrate deleting shoulder peaks according to one embodiment of the present subject matter.

DETAILED DESCRIPTION

An objective of the present subject matter is to provide a method and apparatus to stabilize patterned non-nutritive suck oromotor coordination. Another objective of the present subject matter is to provide an apparatus and method to objectively measure stability a patient's non-nutritive suck. Another objective is to provide a method to assess the efficacy of orosensory entrainment therapy on the emergence of patterned non-nutritive suck in patients with dysfunctional suck using patterned oral cutaneous stimulation intervention.

Figure 1:
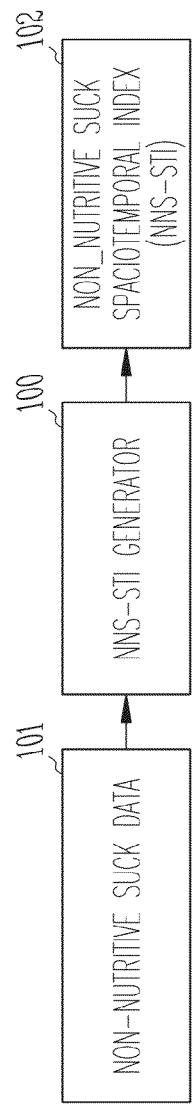
FIG. 1 illustrates an apparatus for determining a non-nutritive suck spatiotemporal index (NNS-STI) according to one embodiment of the present subject matter.

Demonstration of improving NNS requires an objective measure of the physiology of NNS. A physiological approach to the assessment of ororhythmic activity investigates the integrity of the neural circuitry driving the sCPG through an analysis of suck pattern structure and stability. A measurement technique known as the spatiotemporal index (STI), has been used to assess kinematic variability across limb and speech motor trajectories. FIG. 1 illustrates an apparatus for determining a non-nutritive suck spatiotemporal index (NNS-STI) according to one embodiment of the present subject matter. NNS-STI provides a quantitative composite index of non-nutritive suck pattern stability. Mathematically, STI is the cumulative sum of the standard deviations (SD) for a set of trajectories. In various embodiments, NNS STI provides information about an infant's suck which is fundamentally unique from previous measures utilizing feature counts and duration measures on suck cycles or suck bursts. NNS STI quantifies suck over a selected burst pattern epoch. This quantitative approach provides a clinician with a summative index or 'gestalt' of oromotor pattern stability. In a repeated-measures design, the NNS STI provides an inclusive analysis of the emergent ororhythm and suck development. This approach successfully discriminates ororhythmic motor development in patients, such as preterm infants, with progressively severe forms of respiratory distress syndrome. FIG. 1 shows a NNS-STI generator 100 including an input adapted to connect to a data source 101 including non-nutritive suck samples. In various embodiments, non-nutritive suck (NNS) samples include suck data gathered from one or more patients. In general, non-nutritive suck samples include pressure data exhibiting periodic peak waveforms. The STI generator 100 processes the NNS data to generate a non-nutritive suck spatiotemporal index 102. A non-nutritive suck spatiotemporal index 102 provides, among other things, an indication of non-nutritive suck development.

Figure 2:
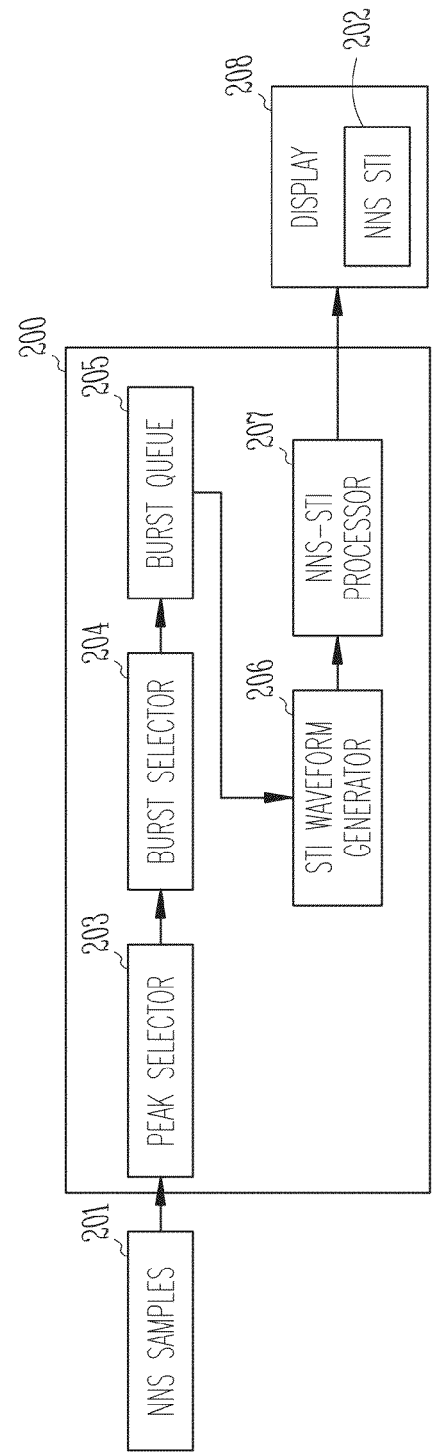
FIG. 2 illustrates an apparatus for determining a NNS-STI according to one embodiment of the present subject matter.

FIG. 2 illustrates an apparatus for determining a NNS-STI according to one embodiment of the present subject matter. FIG. 2 shows an NNS-STI generator 200 including an input adapted to connect to a data source 201 of non-nutritive suck samples. The NNS-STI generator 200 includes a peak selector 203, a burst selector 204, a burst queue 205, a STI waveform generator 206 and a NNS-STI processor 207. In various embodiments, the NNS-STI generator 200 includes an output connection to a display 208 for presenting the NNS-STI 202 and programming parameters for peak selection and burst selection.

In various embodiments, the peak selector 203 allows the user to select peaks within an NNS sample. Peak selection allows identification and selection of NNS bursts. In various embodiments, the peak selector uses the display 208 to provide graphical assistance to the user for selecting peak data points within a NNS sample 201. In various embodiments, peak selection is automated upon selection by the user of criteria, such as a minimum peak threshold, for automatically identifying peaks within a NNS sample of data points.

In various embodiments, the burst selector 204 provides an interface for a user to identify, edit and select burst data for NNS-STI determination. A user selects a burst based on the pattern of selected peaks and a predetermined number of peaks to include in a burst selection. For example, a patient with some NNS development, may exhibit NNS samples with easily identifiable bursts. Such a burst may have 6-8 pressure peaks in each burst. However, a second patient may have a burst identified with only 4 or 5 pressure peaks. In order to compare the relative NNS health of the patients, each patient NNS-STI is based on bursts selected from the NNS data samples with an equal number of peaks. In various embodiments, bursts selected for processing must include at least a minimum number of peaks. In various embodiments, the burst selector allows the operator to delete peaks in selected bursts, such a shoulder peaks indicative of a secondary suck action related to a primary peak. In the illustrated embodiment, selected bursts are stored in a queue 205 for further processing.

In various embodiments, further processing of the queued bursts includes normalizing the data points for each selected burst in both amplitude and time. In various embodiments, amplitude normalization includes determining mean amplitude of the burst data points, determining a number of standard deviations derived from a predetermined number of consecutive data points and dividing each data point by the standard deviation derived using that data point. In various embodiments, time normalization is based on various interpolation methods to extend the sample data over a predetermined number of data points. Linear, rational and spline interpolation are examples of interpolation methods used individually or in combination to time normalize each selected burst.

Time normalized waveforms are input to the STI waveform generator 206 and processed to derive a predetermined number wave points values associated with standard deviation values of the combined normalized selected bursts. The STI waveform generator 206 outputs the wave points to the NNS- STI processor 207 for summation and determination of the NNS-STI 202. In the illustrated embodiment, the NNS-STI is presented on a display 208 attached to the STI generator 200.

Figure 3:
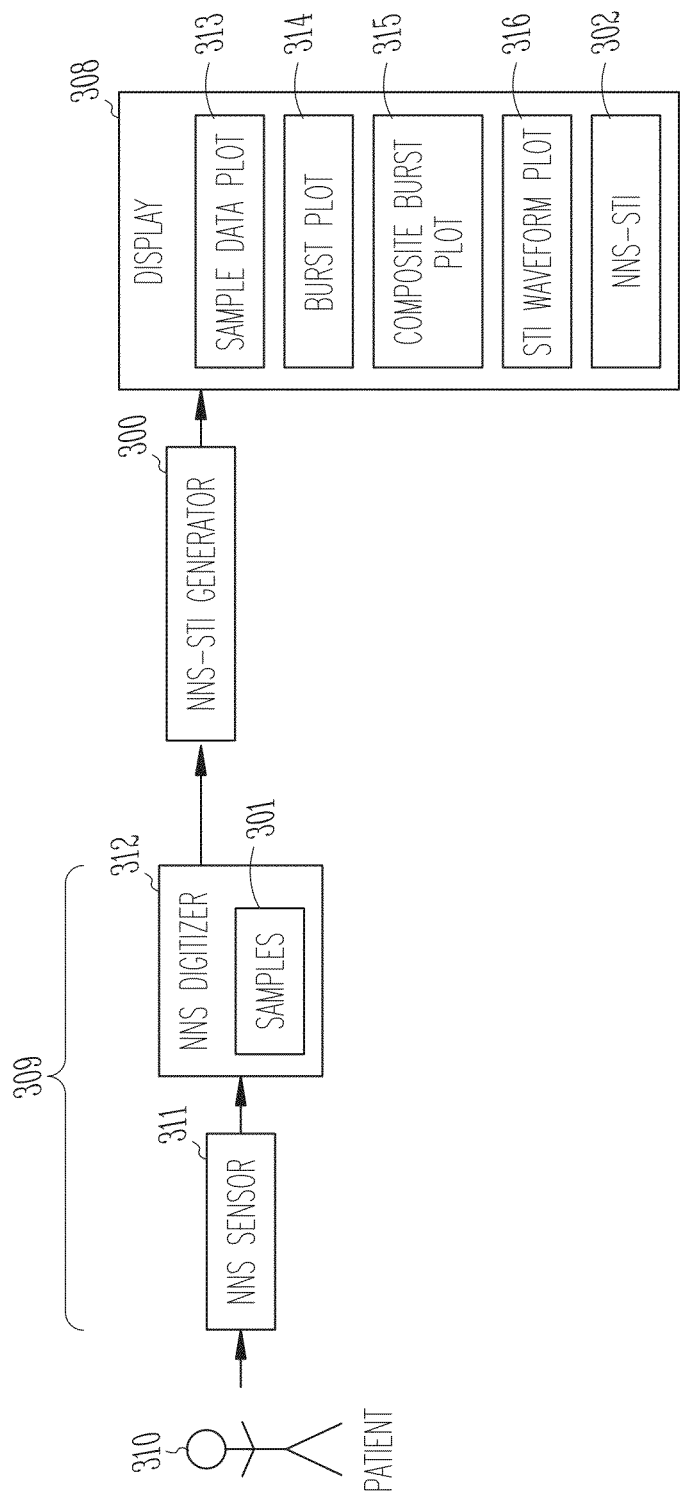
FIG. 3 illustrates a system including an NNS-STI generator 300 according to one embodiment of the present subject matter.

FIG. 3 illustrates a system including an NNS-STI generator 300 according to one embodiment of the present subject matter. The system includes the NNS STI generator 300, a display 308, and a NNS digitizer system 309 for collecting NNS samples from a patient 310. The illustrated NNS digitizer system 309 includes a NNS sensor 311 and NNS digitizer 312 with memory 301 for storing NNS samples. In the illustrated system, the NNS-STI generator 300 is connected to a display 308 and includes functionality to display plots of the sample data 313 input to the NNS-STI generator, plots of burst data 314, composite plots of selected bursts 315, plots of the STI waveform data 316 and presentation of the NNS-STI 302.

Figure 4:
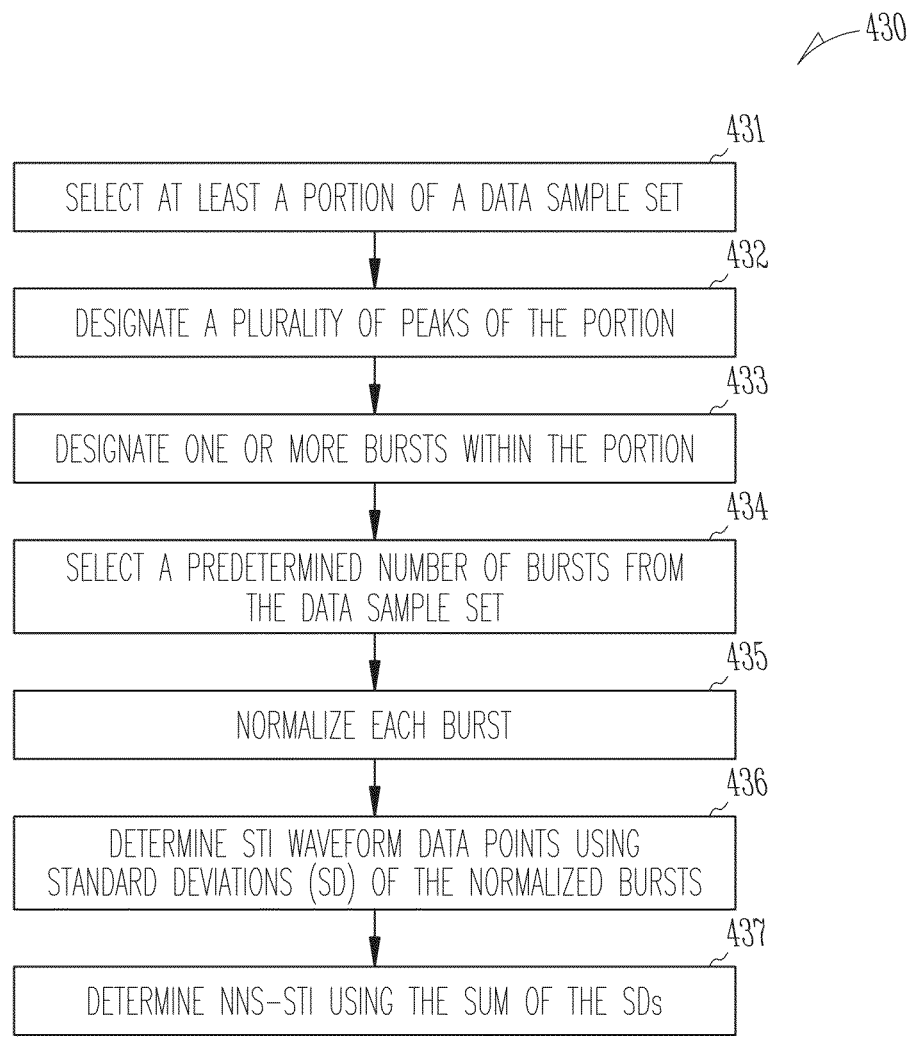
FIG. 4 illustrates a flow chart of a method 430 for processing NNS data to determine a NNS-STI according to one embodiment of the present subject matter.

FIG. 4 illustrates a flow chart of a method 430 for processing NNS data to determine a NNS-STI according to one embodiment of the present subject matter. The process includes selecting at least a portion of data sample set for processing 431, designating a plurality of peaks in the portion of the data set 432, designating one or more bursts in the portion of the data set 433, selecting a predetermined number of bursts from the selected portions of the data sample set 434, normalizing each selected burst upon selection 435, determining STI waveform data points from standard deviations derived from the normalized selected bursts 436 and determining a non-nutritive suck spatiotemporal index from a summation of the derived standard deviations 437.

In various embodiments, selecting a predetermined number of bursts from the selected portion of the data sample set includes selecting additional data sample set portions from data samples collected at the time of the initial data sample set, designating a plurality of peaks in the portion of the data set and designating one or more bursts in the portion of the data set. In various embodiments, selecting a predetermined number of bursts from the data set includes selecting bursts with an equal number of peaks.

FIG. 5 shows a pacifier apparatus 540 according to one embodiment of the present subject matter for use in collecting data samples for generating NNS-STI. A NNS data sample includes digitized NNS compression pressure waveforms recorded using the pacifier apparatus 540. The pacifier apparatus includes a pacifier 541 coupled to a tube 542. The tube is coupled to a pressure transducer, not shown. In various embodiments, the pressure transducer is coupled to a computer and an output signal of the pressure transducer is digitized and recorded in an electronic file, such as a text file. The tension transducer generates an output signal indicative of the pneumatic pressure in the nipple of the pacifier.

In various embodiments, collecting NNS data samples, or trajectories, recorded from an infant includes examining the physiological state of the infant, holding the infant in a developmentally supportive inclined position, dimming any background or overhead lighting to promote eye contact between the infant and the caregiver holding the infant, waiting until the infant is in a optimal behavioral state such as states, 3, 4 or 5 as described by the naturalistic Observation of Newborn Behavior, Newborn Individualized Development Care and Assessment Program, providing the pacifier apparatus for the infant to suck on, and collecting about five minutes of NNS behavior. In various embodiments, the data samples are collected from infants 15 minutes prior to scheduled feeding using a mobile device including the pacifier apparatus and computer running data collection software. NeoSuck RT is an example of data collection software specially designed to record NNS activity. It is understood that other data collection software is possible for collecting NNS data samples without departing from the scope of the present subject matter. Neonatal intensive care patients remain connected to appropriate monitors for observation of respiration, heartbeat and oxygen saturation while collecting the data samples.

Figure 6A:
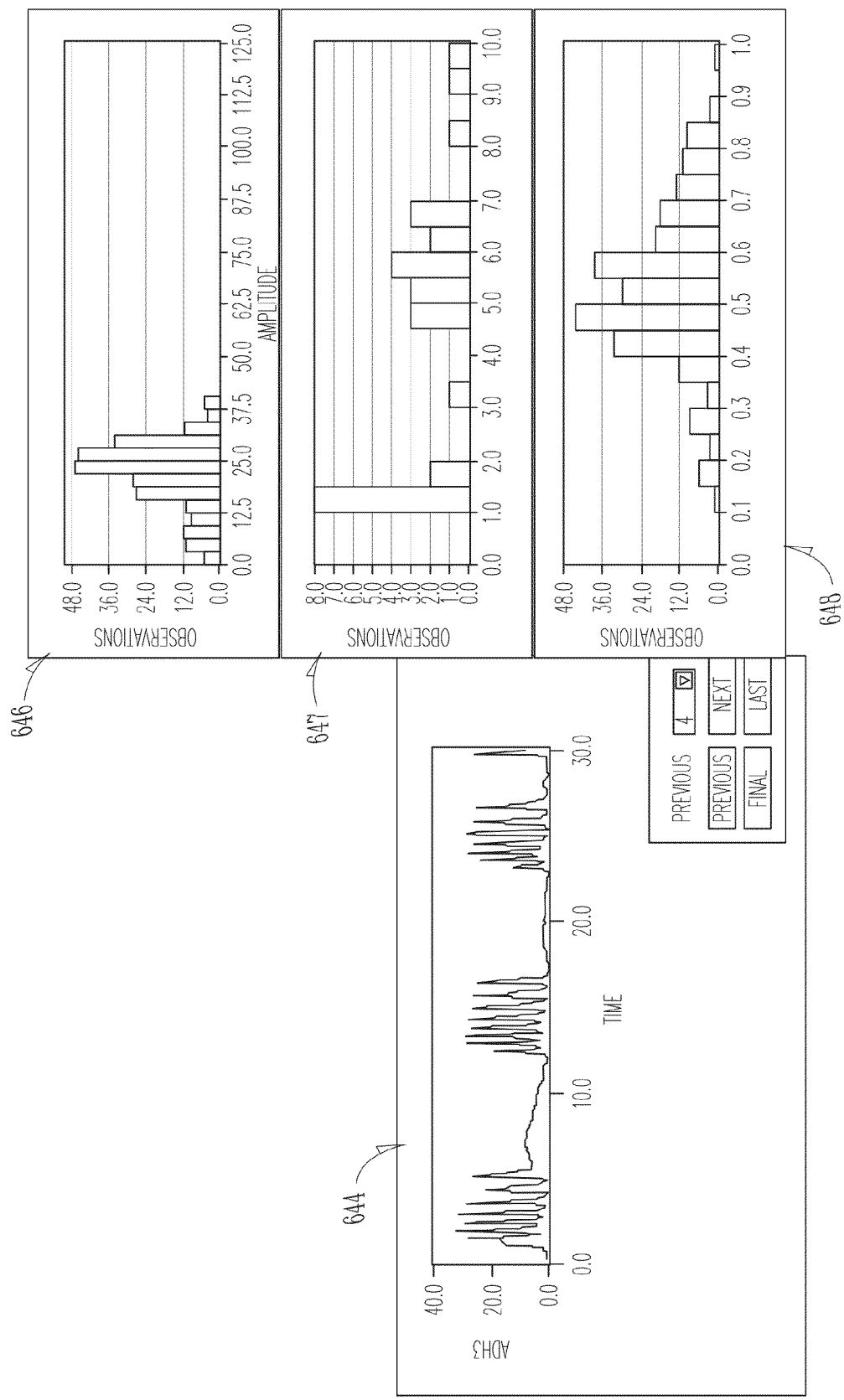
FIG. 6A shows a sample plot 644 of NNS data samples collected using NeoSuck RT for a healthy preterm infant at 35 weeks post-menstrual age (PMA).
Figure 6B:
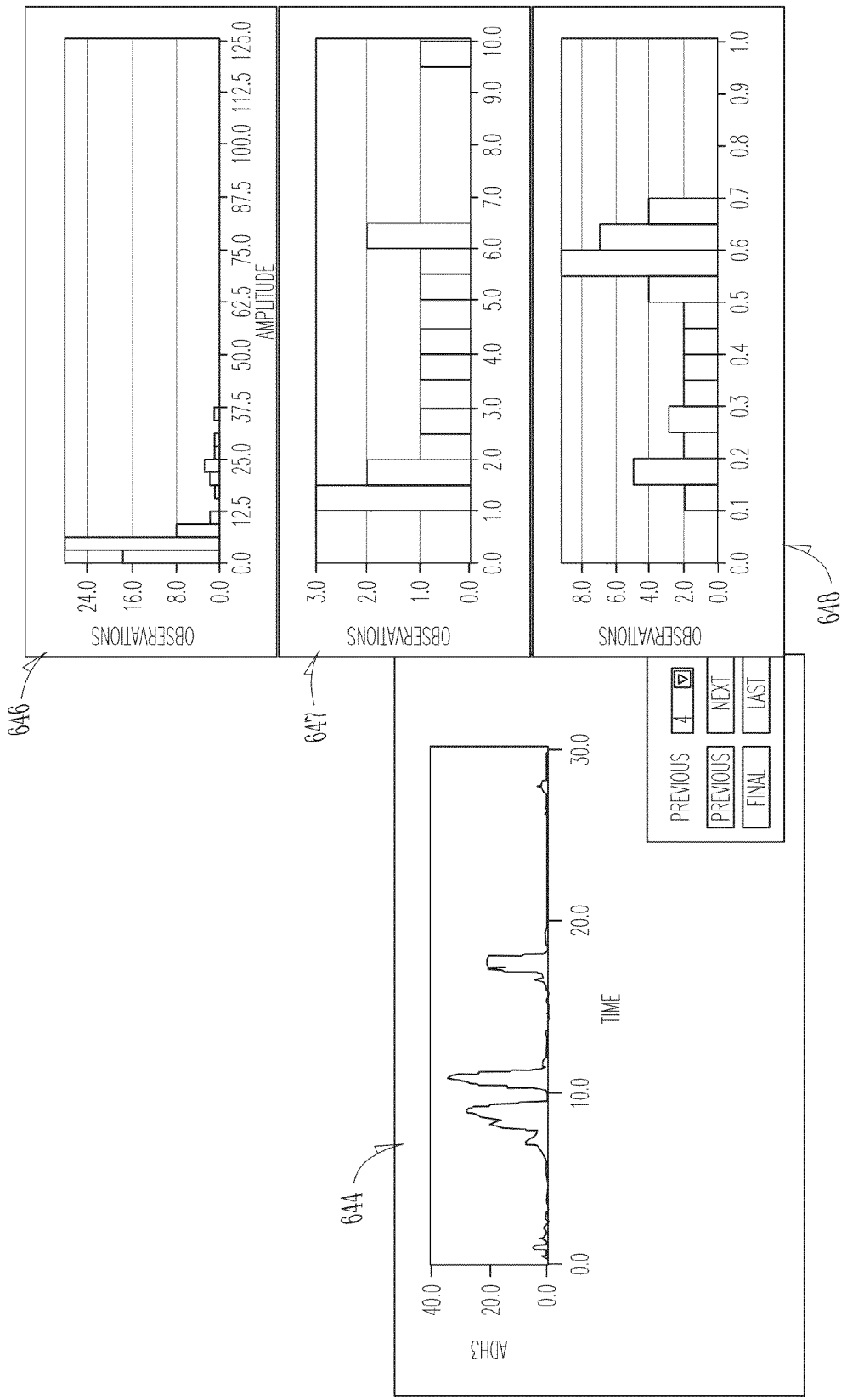
FIG. 6B shows a sample plot of NNS data samples collected using NeoSuck RT for a tube-fed RDS preterm infant at 35 weeks PMA.

FIG. 6A shows a sample plot 644 of NNS data samples collected using NeoSuck RT for a healthy preterm infant at 35 weeks post-menstrual age (PMA). FIG. 6B shows a sample plot of NNS data samples collected using NeoSuck RT for a tube-fed RDS preterm infant at 35 weeks PMA. The real time display 644, 645 provides the clinician with the NNS compression waveform and associated histogram updates for suck amplitude ($cmH_2O$) 646, inter-NNS burst pause periods (sec) 647, and intra-NNS burst suck cycle periods (sec) 648. For the healthy preterm infant, well-organized NNS bursts with peak pressures averaging 25 $cmH_2O$ alternate with pause periods of approximately 5.5 seconds. The NNS cycle count for the complete sample is 251. In contrast, the dissolution of the NNS burst structure for the tube-fed RDS infant corresponds to a disorganized nipple compression pattern and indistinguishable NNS bursts. The amplitude of oral compression output is likewise reduced to approximately 5 $cmH_2O$, with the data collection software able to identify just 65 compression cycles in the total sample of digitized records.

In various embodiments, two minutes of the digitized ororhythmic pressure waveforms with the greatest number of pressure peaks above 1 cm $H_2O$, reflecting an infant's most active period of oromotor output, are selected for NNS STI analysis. In order to measure NNS pattern convergence within each of these samples, suck bursts with a fixed number of peaks (suck cycle) are used. For example, in a typical sample, the first five peaks from five successive bursts are included in analysis. For infants with poorly developed NNS pattern structure, the first five most burst-like mouthing movements are identified, based on period, amplitude, and duration. It is understood that more or less pressure peaks may be selected to form a suck burst without departing from the scope of the present subject matter.

Suck bursts produced by infants often vary in length, peak number, and amplitude. In various embodiments, a NNS STI generator is programmed to initially perform pressure peak detection for each burst and to index the time stamp for each peak. The start- and end-points for a selected NNS burst are calculated by extending the waveform analysis window 300 samples prior to the first peak and 300 samples following the fifth pressure peak to ensure accurate pressure peak waveform discrimination. The five captured bursts are then sequentially normalized in amplitude and time. Time normalization is based on linear interpolation, which projects the five-peak-bursts ensemble to an analysis window based on a preset abscissa scale of 10,000 data samples. Amplitude normalization is accomplished by computing the mean value of each waveform and then dividing the waveform points by the standard deviation for each trajectory. A standard deviation is derived from each increment of 100 points through the 10,000 points of the sampled amplitude data points within the individual suck burst waveform The resultant NNS STI is the cumulative sum of the standard deviations derived from the time and amplitude normalized NNS burst waveforms indexed at 100 ms intervals.

Figure 7:
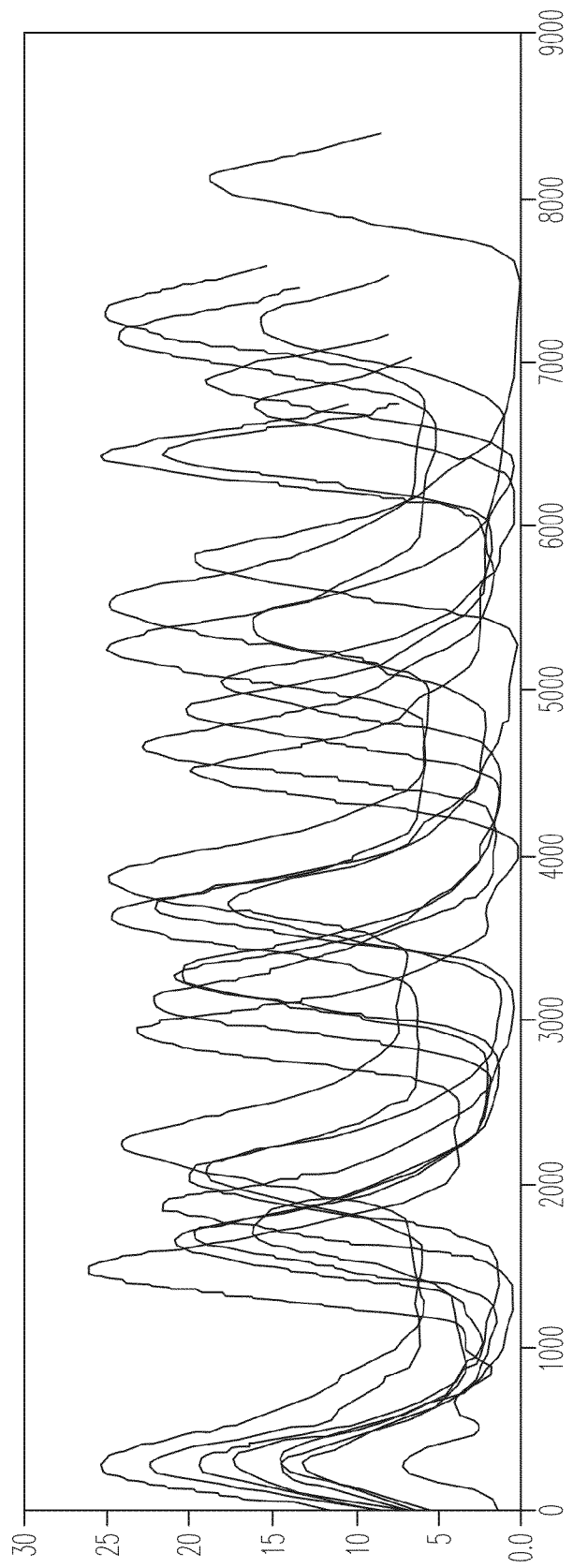
FIG. 7 shows a plot of a plurality of bursts according to one embodiment of the present subject matter.

Mathematically, STI is the cumulative sum of the standard deviations (SD) for a set of trajectories. NNS STI shows the stability of a sequence of movements representing the development of the baby's NNS. In various embodiments, the purpose of non-nutritive suck spatiotemporal index (NNS STI) is to compare the suck pressure control profiles among NNS bursts for comparative studies within and among preterm babies. This comparison is based on a set of selected bursts with fixed peak number. For example, for any individual comparison made, if 5 peaks are selected for the 1st burst, then another 5 peaks must be for the 2nd burst, and always 5 peaks for all the other bursts in this comparison. FIG. 7 shows the first 5 peaks from eight bursts, which are also called trajectories. In various embodiments, selecting the same number of peaks from every burst is necessary to make different sets of trajectories comparable.

Figure 8:
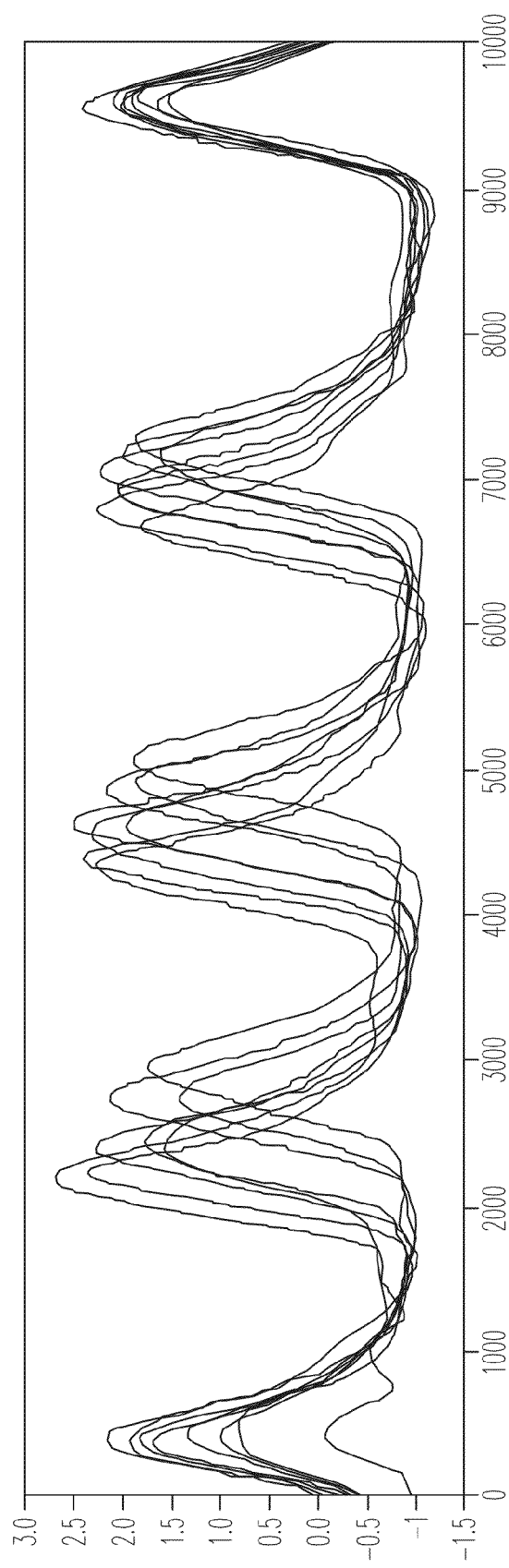
FIG. 8 shows eight normalized trajectories based on the original data in FIG. 7 according to one embodiment of the present subject matter.

As shown in FIG. 7, the five NNS peaks from different bursts have different lengths in term of number of samples. The NNS STI generator normalizes the selected bursts over a predetermined number of samples to generate the index. FIG. 8 shows the eight normalized trajectories based on the original data in FIG. 7 according to one embodiment of the present subject matter. In various embodiments, due to the mathematical requirements of the normalization, the sample number after normalization has to be larger than the maximum non-normalized sample number of each burst. For example, in FIG. 8, the maximum non-normalized data length is around 8500, while after normalization, all the data are lengthened to 10000.

For normalization, suppose a population comprises $x_1, \ldots, x_N$ values. The arithmetic mean of this population is defined as, $$\bar{x} = \frac{1}{N}\sum_{i=1}^{N} x_i = \frac{x_1 + x_2 + \ldots + x_N}{N}$$

and the standard deviation (SD) of this population is defined as, $$\sigma = \sqrt{\frac{1}{N}\sum_{i=1}^{N}(x_i - \bar{x})^2}$$

Figure 9:
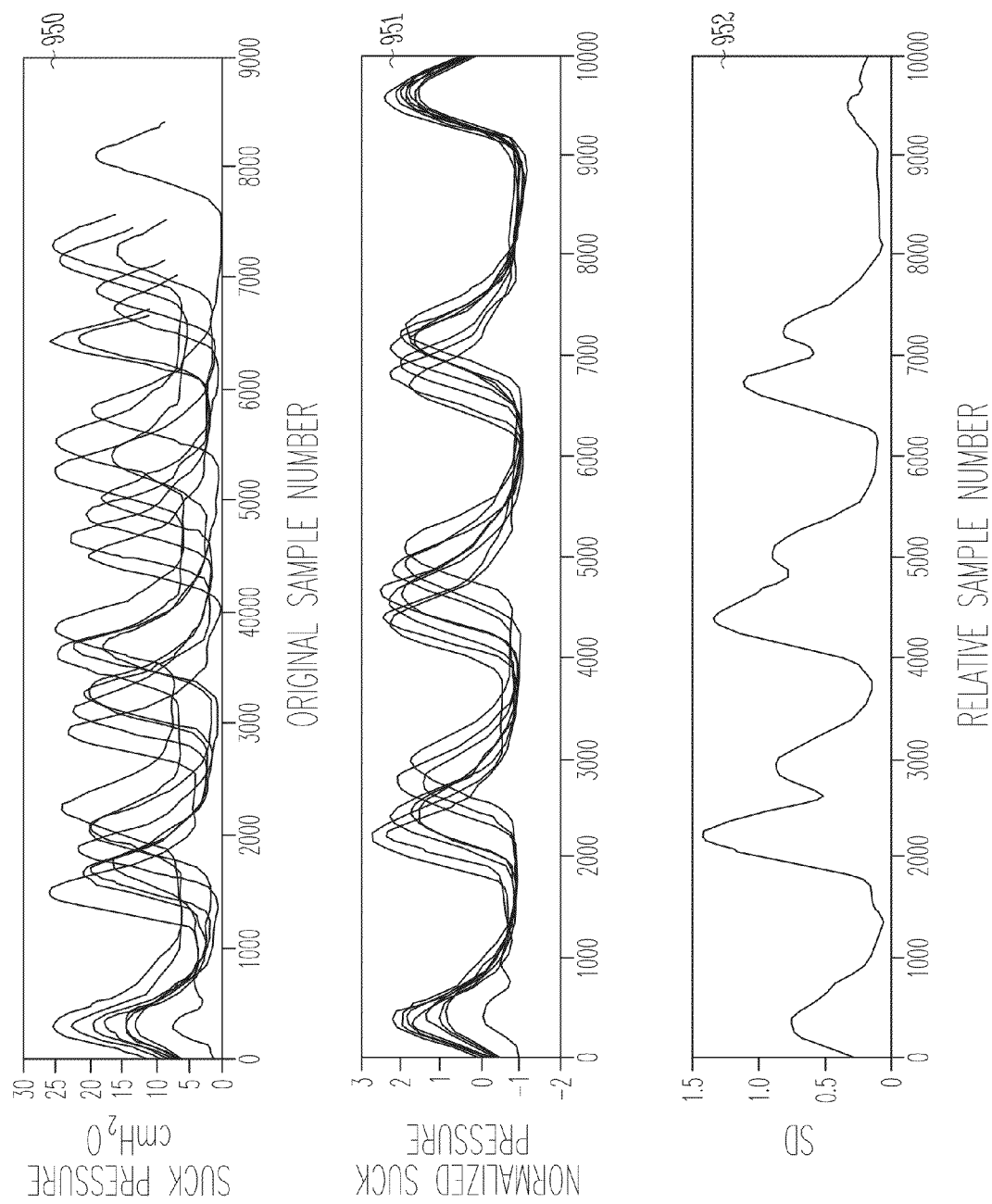
FIG. 9 includes the STI analysis result for a preterm infant with good suck pressure patterning.

As shown in FIG. 7, there are eight trajectories, thus N=8. The SD calculation is then based on eight normalized pressure values for each sample point. In various embodiments, 10000 SD values are calculated for the normalized data. FIG. 9 shows the original data 950, normalized data 951 and standard deviation waveform 952. The STI value represents the sum of standard deviation data points. In various embodiments, SD is added every 100 samples, instead of adding all 10000 SDs.

Figure 10:
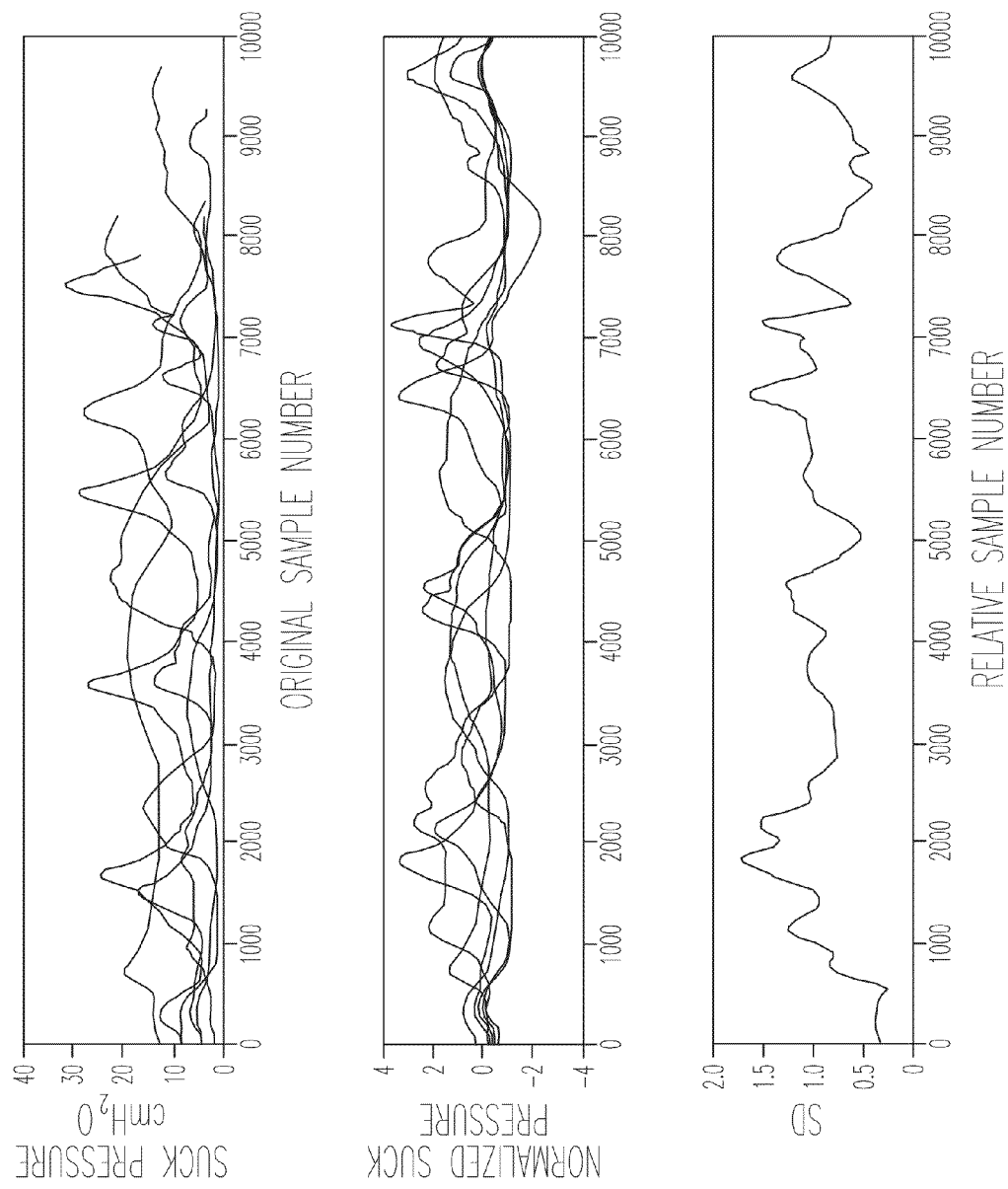
FIG. 10 shows an example of poor NNS patterning sampled from a preterm infant with respiratory distress syndrome

FIG. 9 includes the STI analysis result for a preterm infant with good suck pressure patterning, with an STI=47.60. FIG. 10 shows an example of poor NNS patterning sampled from a preterm infant with respiratory distress syndrome. In this case, the poor suck patterning results in an STI increase to 93.01.

In one embodiment, the NNS STI generator is implemented using a Labview application and input suck pressure data files collected from one or more patients. The next few paragraphs discuss a method for calculating an NNS STI using a particular Labview application embodiment. The discussion assumes the NNS-STI generator includes a display for user interaction with the generator.

Figure 11:
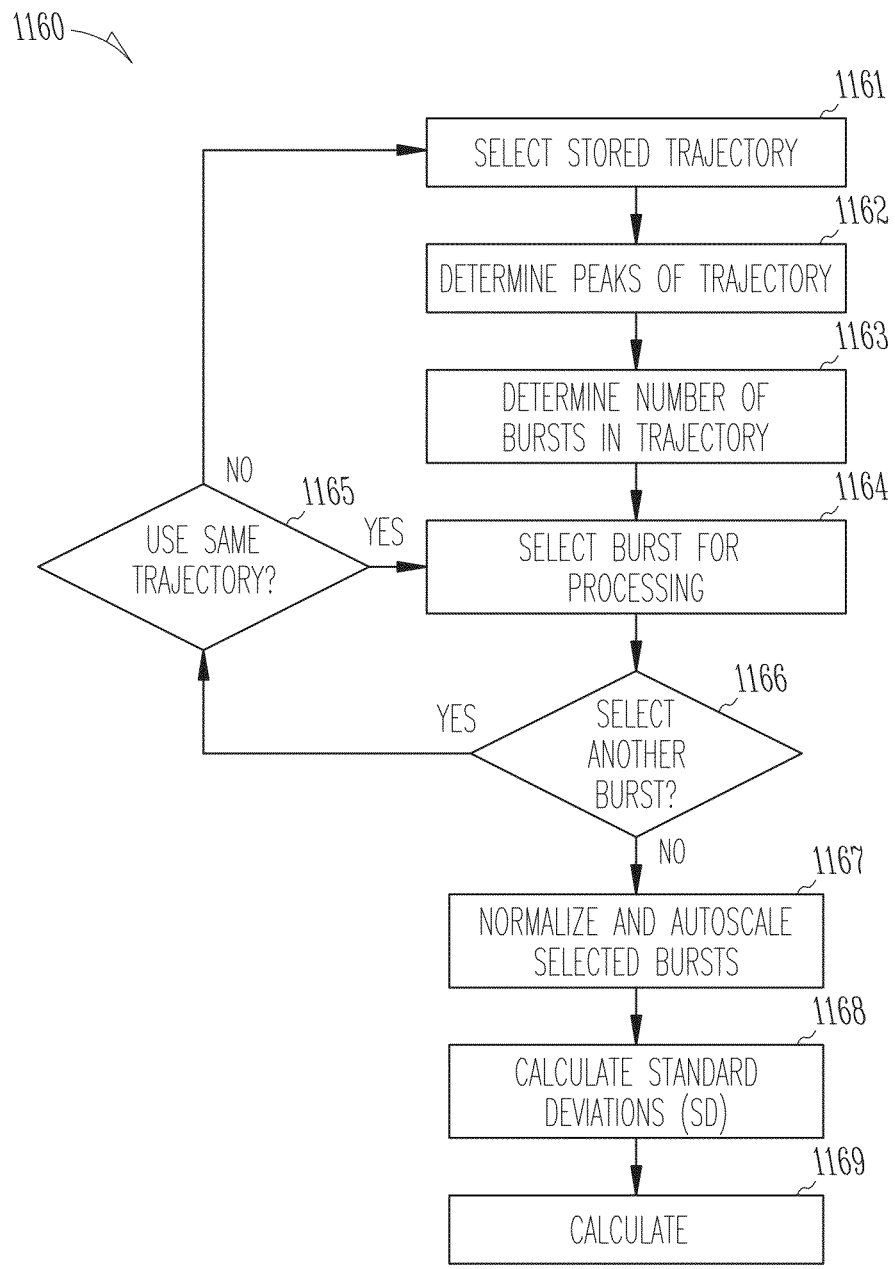
FIG. 11 shows a flow chart of a method for processing data to generate an NNS-STI according to one embodiment of the present subject matter.
Figure 12:
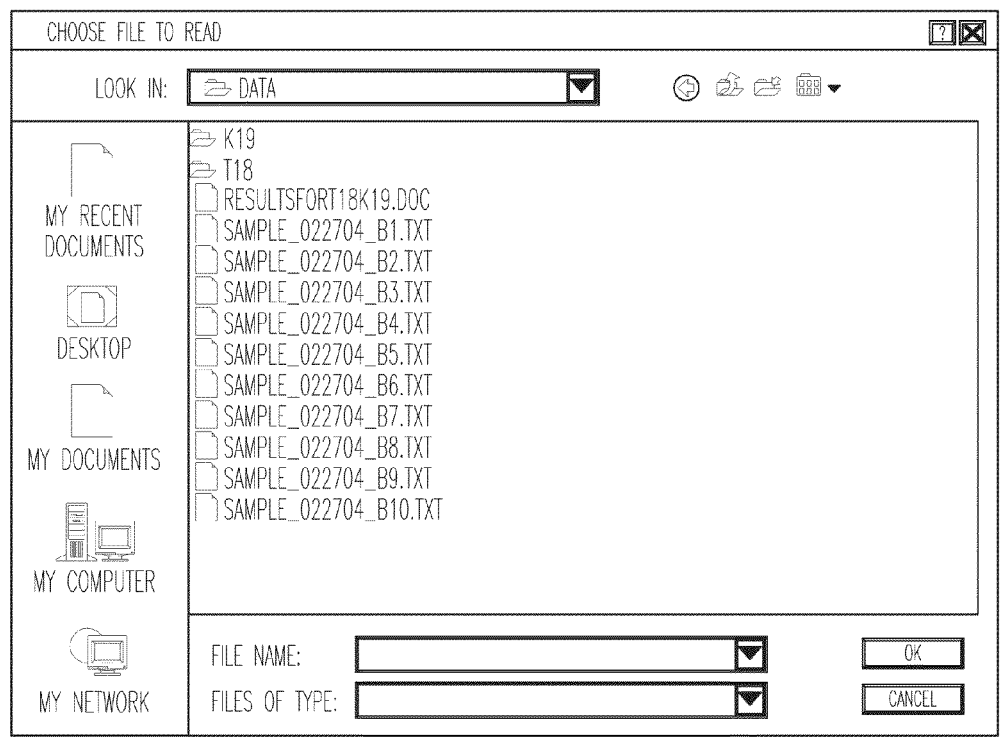
FIG. 12 shows a Choose File dialog box for selecting a stored trajectory according to one embodiment of the present subject matter.

FIG. 11 shows a flow chart of a method 1160 for processing data to generate an NNS-STI according to one embodiment of the present subject matter. The method includes selecting a stored trajectory 1161, determining peaks of the trajectory 1162, determining the number of bursts in the trajectory 1163 and selecting a burst for STI processing 1164. The method further includes determining additional 1166 peaks and bursts from the selected trajectory or a different trajectory 1165, normalizing the selected bursts 1167, calculating a plurality of correlation factors, such as standard deviation 1168, for a plurality of samples using the value of each normalized burst as each of the plurality of samples, and then summing the correlation factors 1169 to form the spatiotemporal index (SPI) for the selected non-nutritive suck trajectories. In various embodiments, the input suck pressure files for NNS STI processing are *.txt files generated from a data collection software package such as NeoSuck RT™. Upon beginning the processing for an NNS-STI, a Choose file dialog box appears requesting the user to select a block of data. FIG. 12 shows a Choose File dialog box for selecting a stored trajectory. After the trajectory is chosen, the suck pressure data is shown in a "Block Suck Pressure" plot. FIG. 13 shows a "Block Suck Pressure" plot 1370 according to one embodiment of the present subject matter. In various embodiments, a red line horizontal threshold cursor 1371 can be tuned (the red line could be dragged up and down) in order to assist in selecting a burst for processing. The cursor helps visualize the primary or dominant peaks 1372 of the trajectory. Peaks with shoulders representing a partial suck peak complicate the NNS STI calculation and the threshold provides a means to suppress a shoulder (should one be present) in the calculation. In various embodiments, peaks recognized and designated for the NNS STI calculation are marked by yellow dots on the display panel. The peak detection algorithm locates the maxima point in the waveform and, in various embodiments, includes criteria related to first and $2^{nd}$ derivatives of the peak waveform.

In various embodiments, bursts are recognized by setting the distance from the last peak position of the first burst to the first peak position of the next burst. Experience of the user is important in recognizing the suck peak cluster constituting an individual burst (as discussed in this example, the burst must have 5 peaks but may also have more than 5 peaks; only the first 5 are included NNS STI calculations). In various embodiments, a user may adjust a "Sample number for distance between bursts" parameter (FIG. 18B, 1881) until a "Number of recognized bursts in current block" parameter (FIG. 18B, 1882) shows the right burst number.

A peak with a peak shoulder may be interpreted as a first and second peak of a burst as shown in FIG. 14A according to one embodiment of the present subject matter. If the sample distance from a peak to its shoulder is less than a "Sample number from peak to its shoulder" parameter (FIG. 18B, 1883), the shoulder is not selected as a peak of a burst. For example, in FIG. 14A, the parameter distance is set to 300 samples and shows the shoulder as a peak as indicated with the dots. While in FIG. 14B, the parameter distance is increased to 900 samples and the selection of the shoulders is deleted.

After the application identifies the peaks in a trajectory, the operator can select one or more bursts from the trajectory for analysis. The operator can select the number of peaks a burst must have for selection by using the "How many peaks you want to compare" parameter (FIG. 18B, 1884). In various embodiments, the application assists in recognizing a burst by using a "Start to 1st Peak" parameter (FIG. 18B, 1885) to identify a pause between bursts. The application identifies the first peak of a potential burst where the peak is not preceded by another peak for the number of samples defined by the parameter. As the parameters and thresholds are adjusted, the application will identify the number of bursts available in the selected trajectory and the operator can sequentially select one or more of the identified bursts for processing. In various embodiments, as each burst is selected, it is plotted in a separate window of the application. In various embodiments, the "selected length for comparison" parameter (FIG. 18B, 1886) assists the user in fine tuning the number of samples to include for each selected burst.

Figure 15:
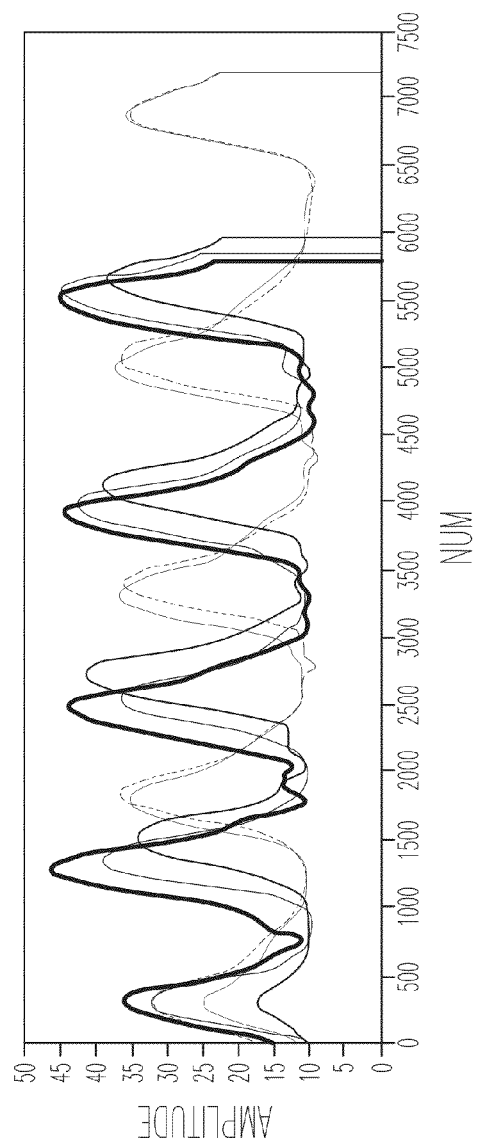
FIG. 15 shows a plot of selected bursts peaks according to one embodiment of the present subject matter.

FIG. 15 shows a plot of selected bursts according to one embodiment of the present subject matter. Upon selection of the bursts, the data is normalized and re-plotted. In various embodiments, normalizing the data points for each selected burst includes normalizing the data with respect to both amplitude and time. In various embodiments, amplitude normalization includes determining mean amplitude of the burst data points, determining a number of standard deviations derived from of a predetermined number of consecutive data points and dividing each data point by the standard deviation derived using that data point. In various embodiments, time normalization is based on various interpolation methods to extend the sample data over a predetermined number of data points. Linear, rational and spline interpolation are examples of interpolation methods used individually or in combination to time normalize each selected burst.

Figure 16:
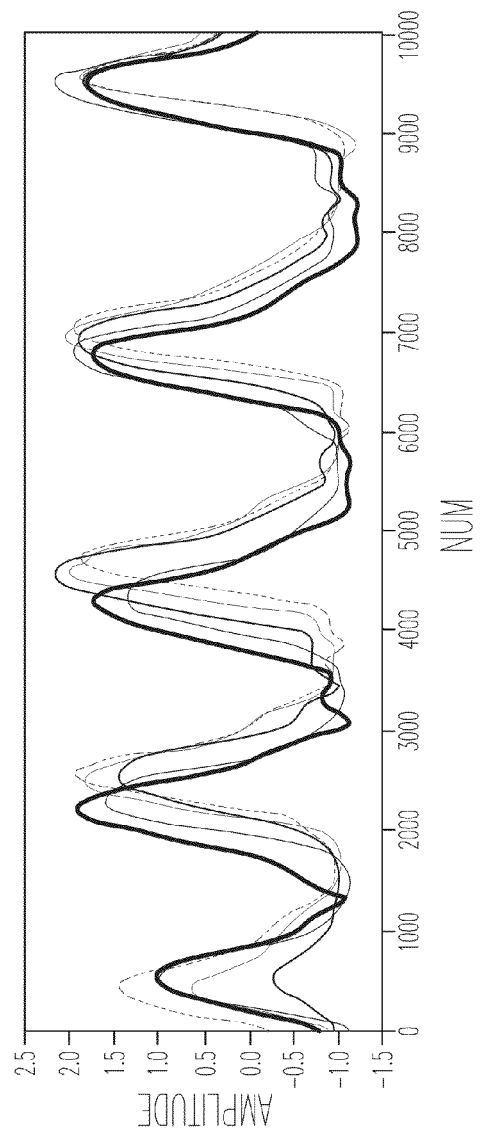
FIG. 16 shows a plot of the selected bursts of FIG. 15 normalized over 10000 sample points according to one embodiment of the present subject matter.

FIG. 16 shows a plot of the selected bursts of FIG. 15 normalized over 10000 sample points according to one embodiment of the present subject matter. In various embodiments, the number of samples over which to normalize selected bursts must be more than the number of samples in each selected burst (FIG. 18B; 1886).

Figure 17:
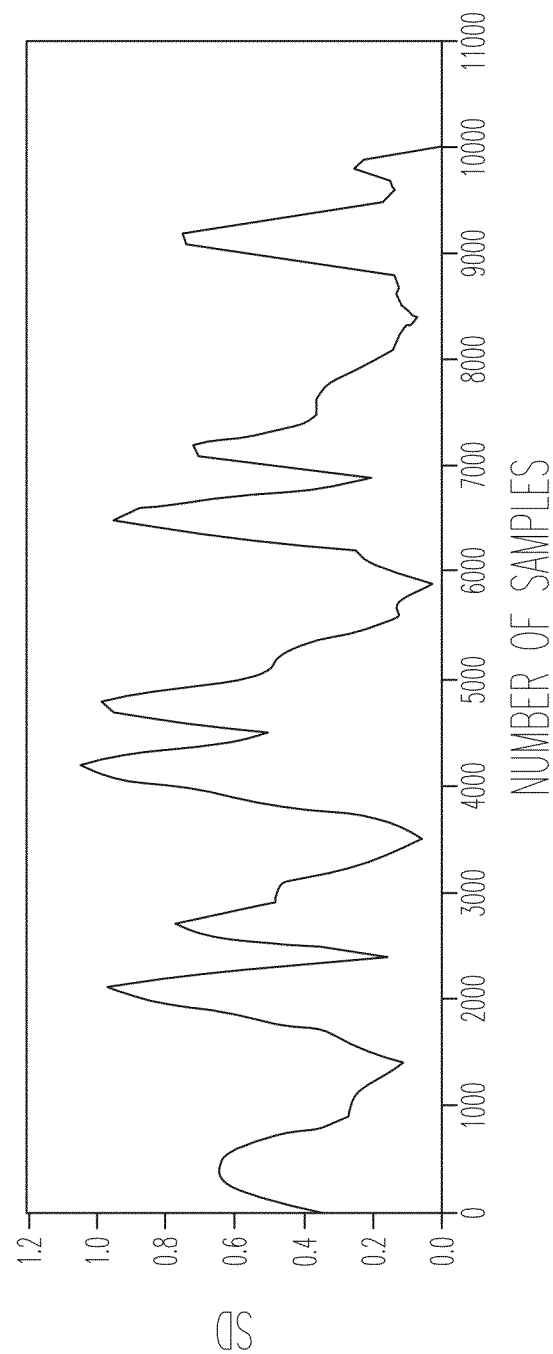
FIG. 17 shows a plot of the SD waveform for the bursts of FIG. 16 according to one embodiment of the present subject matter.

In various embodiments, correlation value such as, a standard deviation (SD), is calculated for each normalized data point across the selected number of trajectories. In some embodiments, a "SD_Step" parameter (FIG. 19A,B; 1991) allows the SD to be calculated once for every SD_Step normalized samples. For example, if SD_Step is equal to 100, SD will be calculated once for each 100 normalized samples, thus reducing the complexity of the calculation for the NNS-STI. FIG. 17 shows a plot of the SD waveform for the bursts of FIG. 16 according to one embodiment of the present subject matter.

Figure 18A:
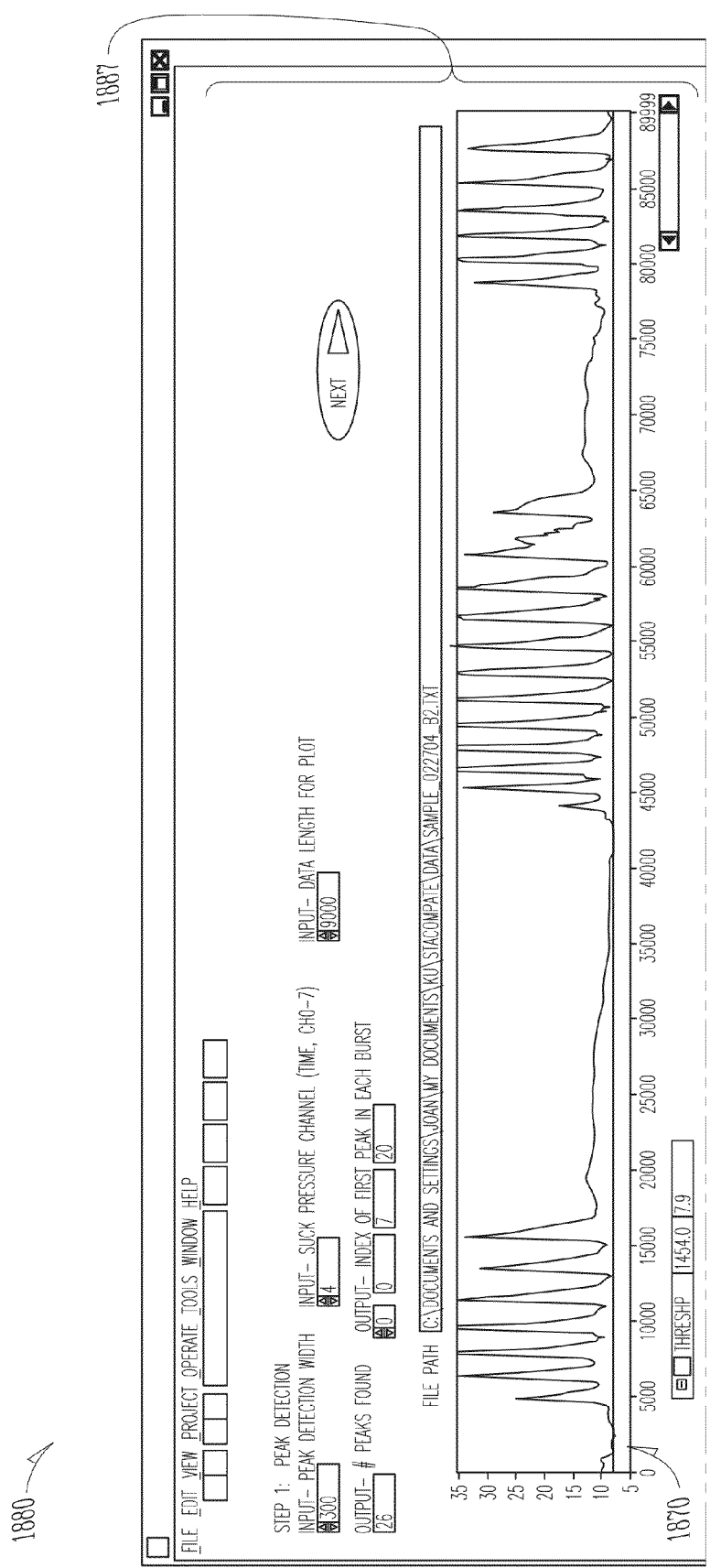
FIGS. 18, 19A and 19B show screen shots for interfacing with an NNS STI generator according to one embodiment of the present subject matter.
Figure 18B:
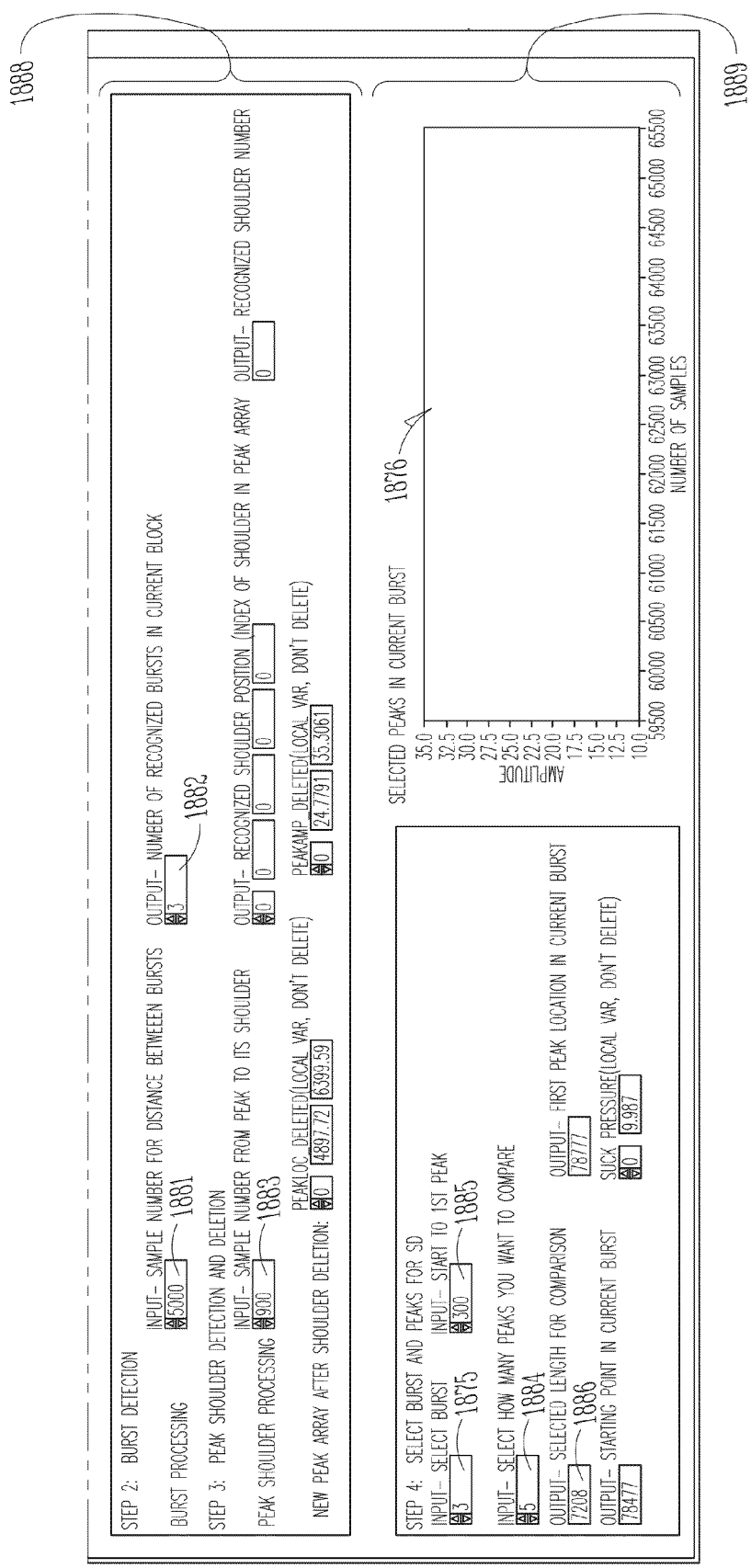
Figure 19A:
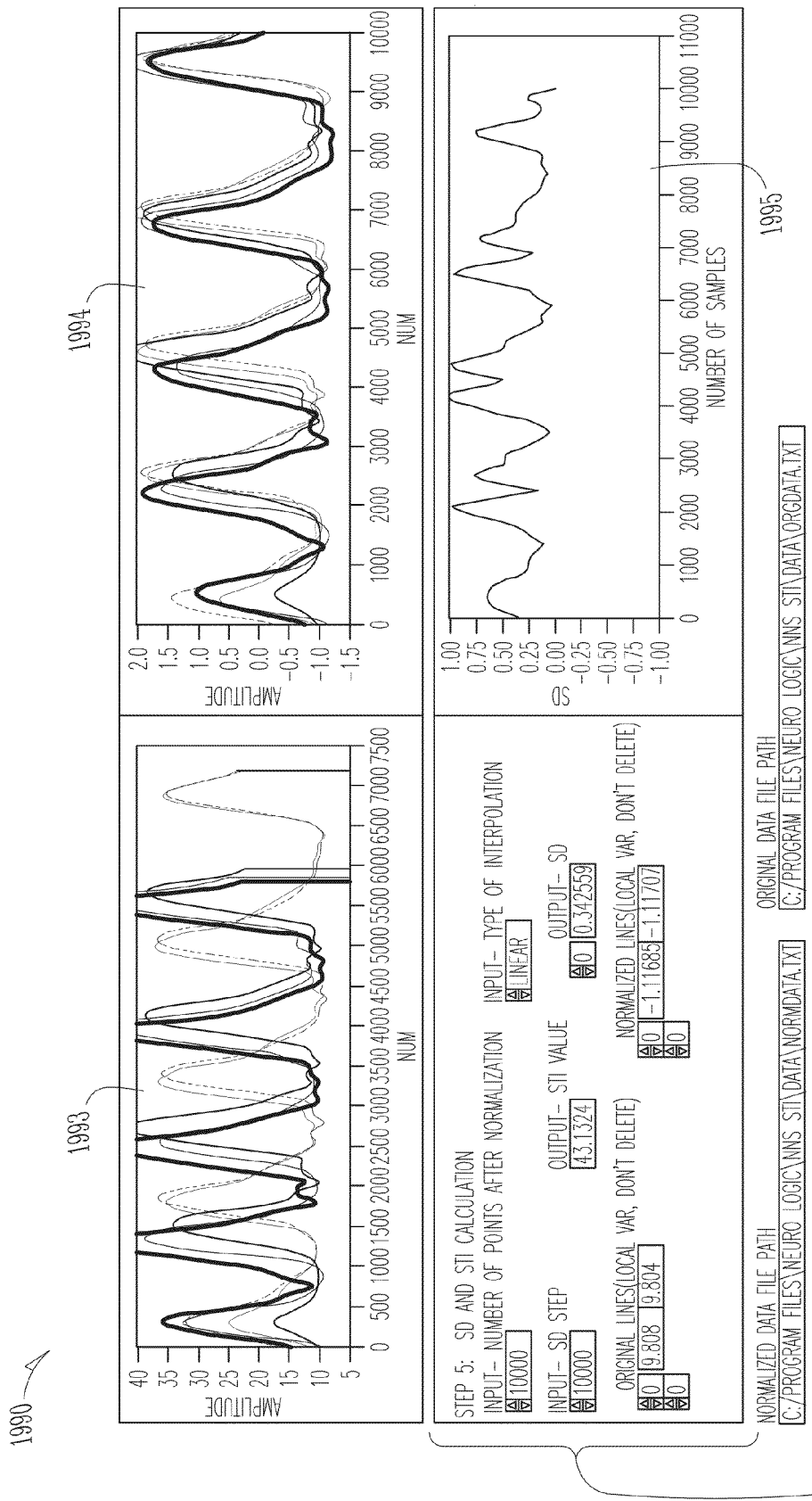
Figure 19B:
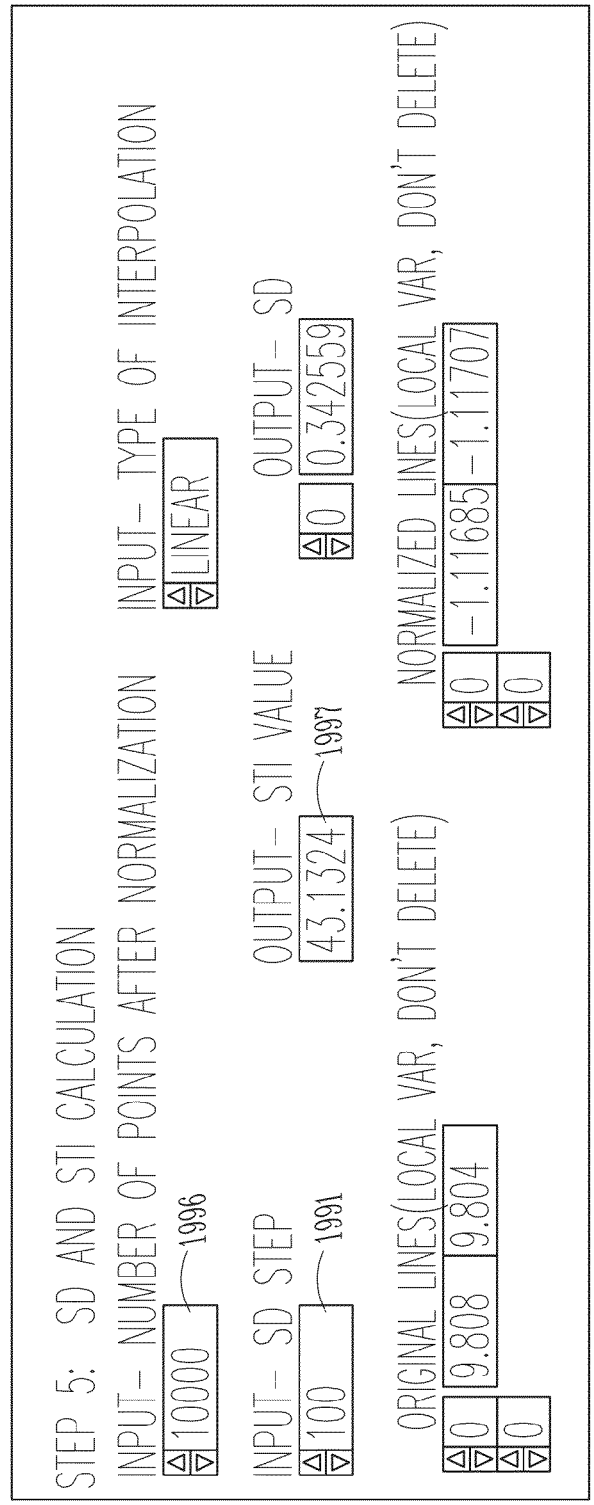

FIGS. 18, 19A and 19B show screen shots for interfacing with an NNS STI generator according to one embodiment of the present subject matter. FIGS. 18A and 18B, combined, show a screen shot of NNS STI generator display interface 1880 according to one embodiment of the present subject matter. The screen shot 1880 includes an area to assist with peak detection 1887, an area to assist with burst detection and peak shoulder detection 1888 and deletion and an area to assist with burst selection 1889. The peak detection area shows a plot of recorded non-nutritive suck data 1870 and includes a threshold line 1871 to help identify pressure peaks in the data. The burst detection and peak shoulder detection and deletion area 1888 includes inputs for selecting the sample interval between a last peak of a first burst event and a first peak of a second burst event 1881. The area 1888 also includes an output parameter showing the number of identified bursts in the selected non-nutritive suck data 1882. The area 1888 also includes an input for preventing shoulder peaks from being recognized as primary pressure peaks in a burst 1883. The burst selection area includes an input to select a particular burst event in the selected non-nutritive suck data 1875, a input to assist in distinguishing between burst events 1885 and a input to select a minimum number of pressure peaks to include in a selected burst 1884. The area also includes a plot of the selected bursts 1876. FIGS. 19A and 19B shows a screen shot 1990 and a portion of the screen shot 1992 related to the selected bursts and the spatiotemporal index according to one embodiment of the present subject matter. FIG. 19A shows a screen shot 1990 including plots of the selected bursts 1993, a plot of the normalized bursts 1994 and a plot of standard deviations derived from the normalized bursts 1995. FIG. 19B shows a detail 1992 of the SD and STI parameters associated with the selected bursts. The area includes an input to select the number of samples over which to normalize the duration of each of the selected bursts 1996 and an input to select the sample step (SD_Step) to use in generating the standard deviation data 1991. In the illustrated embodiment, the selected bursts are normalized over 10000 samples. The SD Step parameter is set to 100, thus 100 (i.e. 10000/100) standard deviations will be generated for the selected bursts. The area also presents the generated NNS STI for the selected bursts 1997.

The inventors have discovered that the sCPG can be modified by peripheral input arising from oral mechanoreceptors which encode the consequences of oral movements along central pathways of the trigeminal system. Mechanosensory stimulation delivered to the baby's oral sensorium can entrain the sCPG. Entrainment is a powerful method of achieving neural synchrony among sensorimotor pathways. Entrainment therapy including patterned oral cutaneous stimulation can assist in organizing NNS. The NNS STI represents an efficient measurement tool to document a therapy of patterned oral cutaneous stimulation's ability to 'jump-start' and shape non-nutritive suck development. Patterned orosensory stimulation is highly effective in accelerating the development of ororhythmic motor output in preterm infants with delayed or disordered suck and poor feeding skills. Reductions in the spatiotemporal variability of NNS following patterned oral cutaneous stimulation treatment reflect an improvement in the brain's ability to organize the ororhythmic motor system for non-nutritive patterning. This skill appears to be an important adjunct Or precursor to the higher order complexities involved with oral feeds, and may even predict success in later-developing oromotor skills, such as mastication, babble, and speech.

The NNA STI provide clinicians with a single numerical value indicating the stability of NNS or oromotor sequence of a patient such as an infant. A higher NNS STI value indicates a poor suck burst pattern formation, whereas a lower value indicates suck burst pattern stability.

Figure 20:
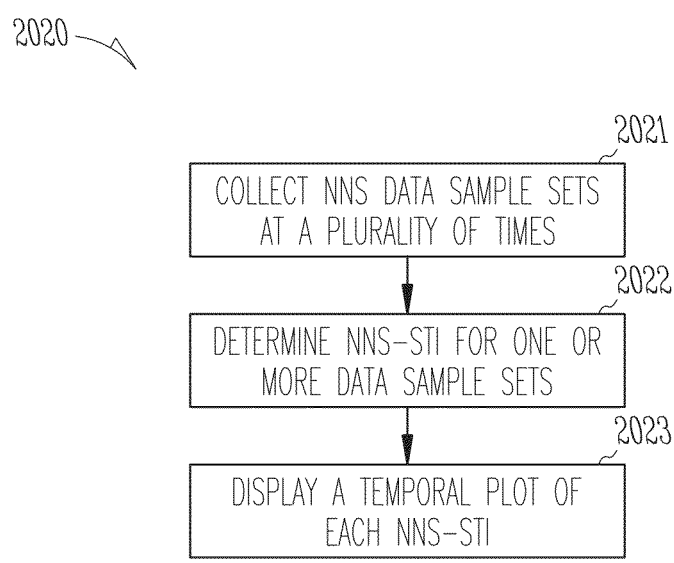
FIG. 20 illustrates a flow diagram for monitoring NNS entrainment progress using NNS-STI data according to one embodiment of the present subject matter.

In various embodiments, improving NNS via analysis of the NNS using the NNS STI begins with evaluating the condition of a patient. Improving NNS STI scores is common for infant patients, however, improvement is possible for older patients with diminished NNS or nutritive suck capacity as well. FIG. 20 illustrates a flow diagram for a method 2020 monitoring NNS entrainment progress using NNS-STI data according to one embodiment of the present subject matter. The illustrated process includes collecting non-nutritive suck (NNS) data sample sets at a plurality of times 2021. In various embodiments, NNS data is collected monthly. In various embodiments, NNS data is collected weekly. In various embodiments, NNS data is collected daily. The illustrated process further includes determining an NNS-STI for one or more of the collected data sets 2022 and presenting a temporal plot of the determined NNS-STIs 2023.

In various embodiments, evaluation, or sampling, of NNS data for an infant patient includes collecting digitized NNS nipple compression pressure waveforms on a daily or weekly schedule from the infant at crib side 15 minutes prior to feeding using the mobile data acquisition system including data acquisition software such as NeoSuck RT™ software.

In various embodiments, an apparatus for collecting digitized NNS nipple compression pressure waveforms includes a sterile pacifier coupled to a receiver instrumented with a pressure transducer, for example a Honeywell pressure transducer (DC-coupled, LP Butterworth @ 50 Hz, 3 Ksamples/sec). A Soothie™ silicone pacifier (Children's Medical Ventures, Inc.) is an example of a typical pacifier used with a pressure transducer for sampling an infant patient.

Following a brief examination of physiologic state, the infant is held in a developmentally supportive inclined posture consistent with the Newborn Individualized Developmental Care and Assessment Program (NIDCAP; 21). Three minutes of NNS behavior is digitally sampled for the infant per session. The data is saved as a digital waveform (suck profile) for subsequent processing in which suck bursts are selected for the NNS STI Index calculation.

Figure 21:
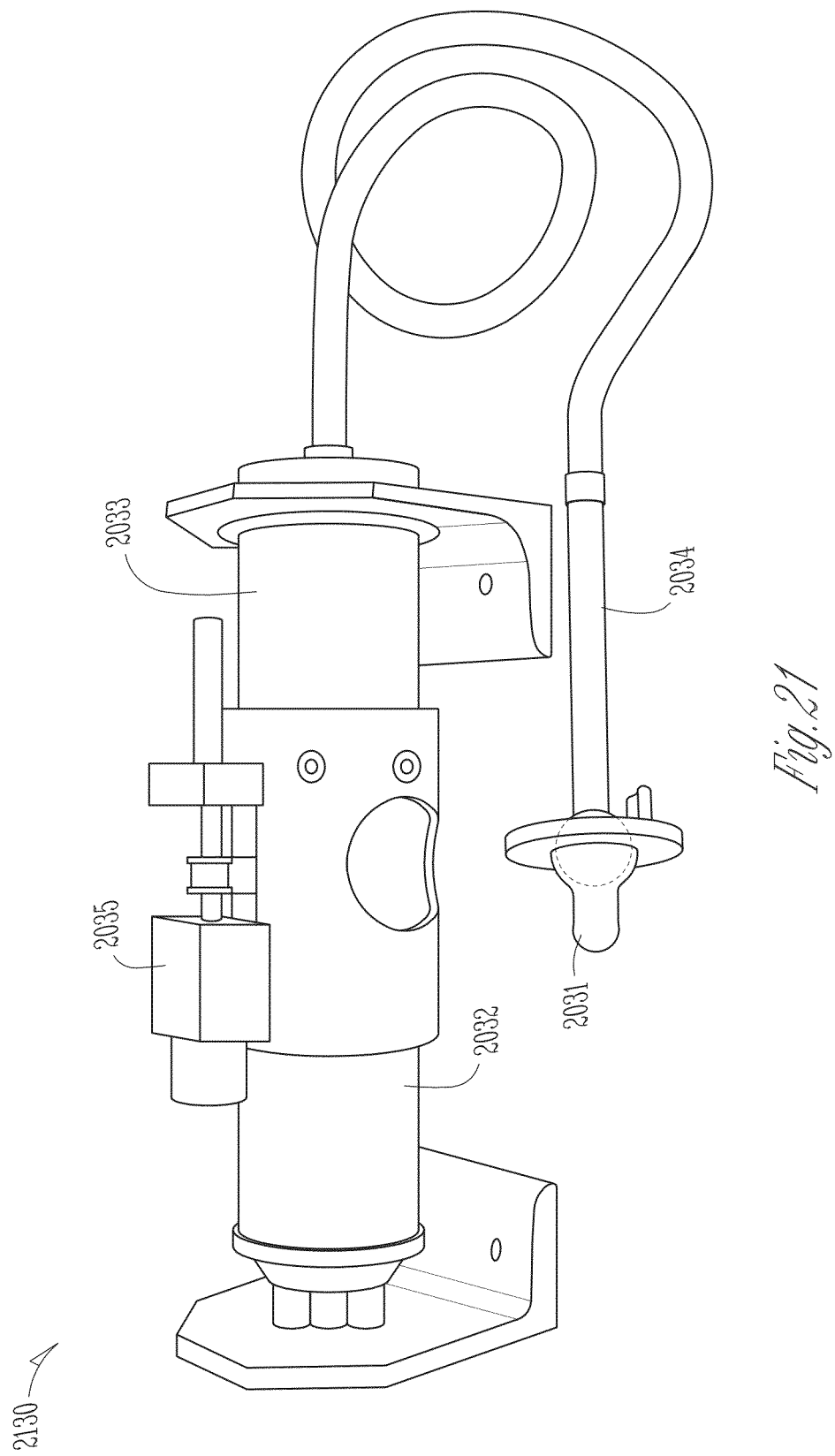
FIG. 21 shows a device for delivering patterned oral cutaneous stimulation according to one embodiment of the present subject matter.

In various embodiments, NNS entrainment therapy includes a patient, such as an infant, receiving 3-minute epochs of patterned oral somatosensory stimulation during gavage feeds. The patterned oral cutaneous stimulation is programmed to mimic the temporal features of NNS. In various embodiments, precision stimulus control is achieved with a servo-controlled linear motor operating under position feedback and coupled in series with a pressurized actuator. FIG. 21 shows a device 2130 for delivering patterned oral cutaneous stimulation according to one embodiment of the present subject matter. A synthetic pulse train input is used to dynamically modulate the intraluminal pressure and conformation (shape) of an infant's preferred Soothie™ silicone pacifier 2031. The device includes a servo linear motor (H2W Technologies, Inc.) 2032 operating under position feedback and coupled in series with a pneumatic Airpel® actuator 2033 and the pacifier receiver 2034. The device includes an MTS® sensor 2035 for position feedback control, which provides for precision stimulus control. In various embodiments, a 16-bit digital-to-analog converter is used to create a synthetic NNS train which consists of a series of 6-cycle bursts and 2-second pause periods. Individual cycles within-burst are presented at 1.8 Hz. The resulting dynamic changes in intraluminal pressure yields a radial expansion of the pacifier nipple of approximately 135 microns with a 25 millisecond rise/fall time. This unique instrumentation transforms the infant's pacifier into an active stimulator or "pulsating nipple" which mimics the temporal pattern of a typical NNS burst. NTrainer System™ is an example of a device for providing patterned oral cutaneous stimulation. In various embodiments, a total of 34 synthetic NNS burst-pause trains are presented to the infant during a single 3-minute stimulation session. Infants receive the stimulus three to four times per day during scheduled gavage feeds over a 10-day period, or until the infant attained 90% oral feeds for two consecutive days.

Figure 22A:
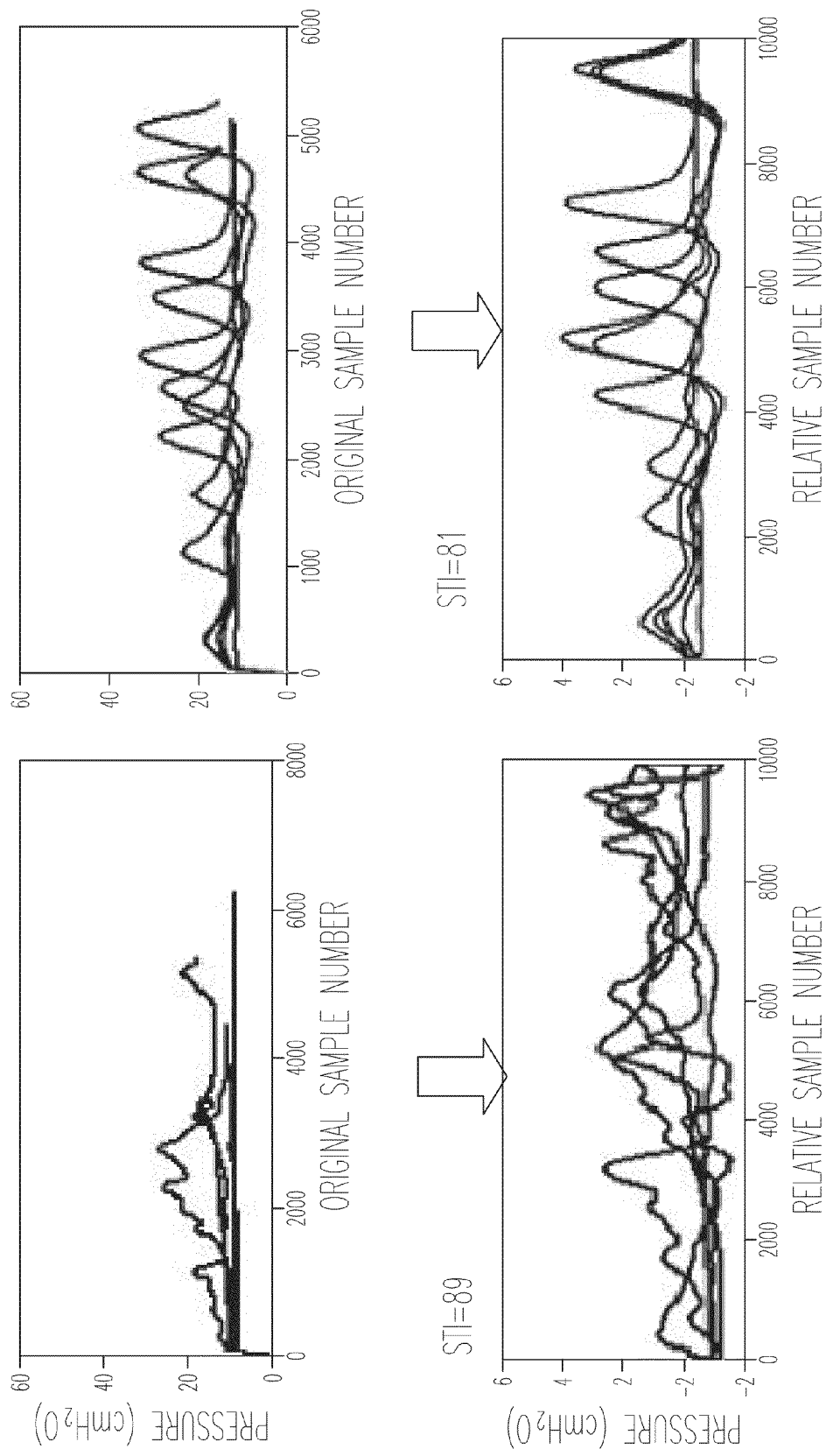
FIGS. 22A and 22B illustrate results of a study for improving NNS in a number of infants.
Figure 22B:
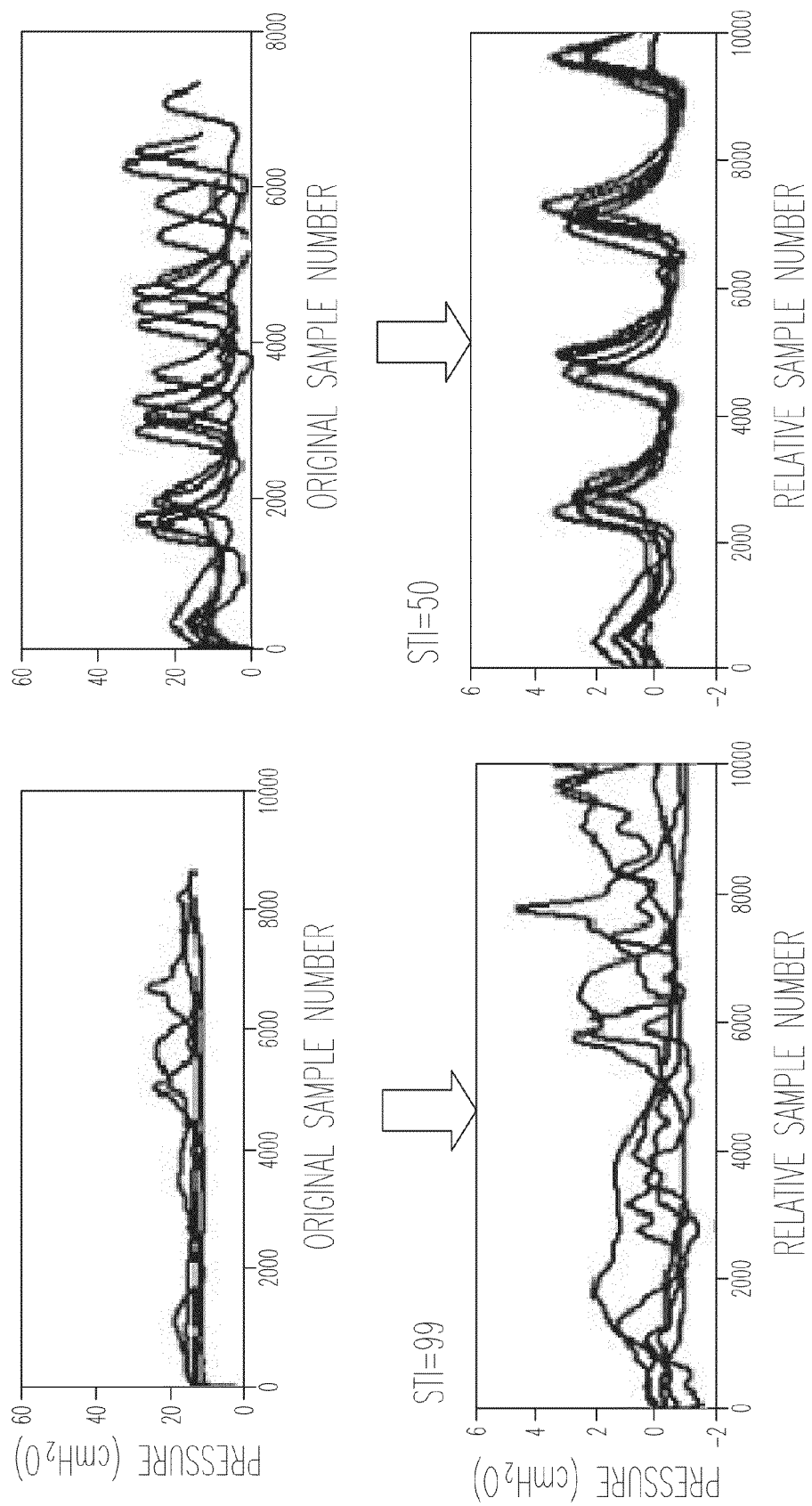

FIGS. 22A and 22B illustrate results of a study for improving NNS in a number of infants. The study assessed NNS of the subjects, divided the subjects into a control group and stimulation group, applied patterned oral cutaneous stimulation to the subjects in the stimulation over a ten over a ten day period and assessed each subject of both groups using NNS STI about three weeks after beginning the stimulation. An article titled "*Synthetic Orocutaneous Stimulation Entrains Suck in Preterm Infants With Feeding Difficulties*" by S. M. Barlow et al. (Neonatology Today, vol. 3: 4, April 2008) discusses the study and is incorporated herein by reference in its entirety.

Infants assigned to the stimulation group received alternating 3-minute epochs of patterned oral somatosensory stimulation during gavage feeds using a stimulation device. The patterned oral cutaneous stimulation mimics the temporal features of NNS. A total of 34 synthetic NNS burst-pause trains were presented to each infant during a single 3-minute stimulation session. Infants were typically treated with stimulation three to four times per day during scheduled gavage feeds over a 10-day period, or until the infant attained 90% oral feeds for two consecutive days.

A statistical analysis procedure, such as (Statistical Analysis System v.9.1.3, PROC MIXED, was used to conduct a Multilevel Analysis using NNS STI as the response variable in the study of preterm infants. In the study of 31 pre-term infant subjects, the relation between developmental phase (pre-stimulation/early PMA vs. post-stimulation/late PMA) and group (stimulation treatment infants vs. no-treatment control infants) was examined. In order to compare the NNS STI scores of treated infants and controls, the controls were age-matched to the treated infants' pre- and post-stimulation PMAs. Treated infants had a mean PMA of 35.1 weeks pre-stimulation and 37.5 weeks post-stimulation. The mean of these (36.4 weeks PMA) served as a division point for the control infants' sessions. Thus, weekly NNS STI scores obtained before 36.4 weeks PMA were "pre" scores, and scores after 36.4 weeks PMA were "post" scores.

Once divided into pre and post groups, infants in both the treatment and control groups had a single early-PMA and a single late-PMA NNS STI score. These values are either an average of NNS STI scores across two weekly sessions (mean=7.85 days apart, SD=5.64) or one session in infants who were unstable or undergoing other medical treatments at the time the second session would have been obtained. Due to factors including ill health status and transferring to another hospital, two control infants did not have early-PMA NNS STI scores, and one control infant did not have a late-PMA NNS STI score.

Covariates included birth GA, birth weight, and PMA at session. A correlation coefficient was calculated for STI, PMA at session, birth GA, and birth weight. Because birth GA and birth weight were found to be highly correlated (0.761), and birth GA had a relatively higher correlation with STI than birth weight (birth GA=0.112; birth weight=0.039), birth weight was excluded from the model. In addition, early PMA and late PMA ages were similar, so co-linearity in the model was avoided by using post-test PMA values across both measures.

Mixed model multilevel analysis reveals significant effects for developmental phase (pre-Stimulation/early PMA vs. post-stimulation/late PMA) $[F(1,26)=65.37, p<0.0001]$ and group (stimulation vs. control infants) $[F(1,26)=6.18, p=0.019]$. Both stimulation-treated and control infants entered the study with similar NNS STI scores, but treated infants demonstrated a significant and disproportionate improvement in their NNS STI scores.

Infants who received stimulation intervention manifest significantly improved NNS STI scores as a function of the patterned orosensory treatment: mean STI=85.07 (SD=9.96) before treatment and 56.52 (SD=11.65) after treatment (FIG. 2). This represents a 39.9% decrease in NNS STI. The relation between the effects of stimulation intervention and the disproportionate decrease in STI values is represented by the highly significant interaction between phase and group $(F[1, 26]=11.51, p=0.002)$. Models including the interactions of PMA by index, PMA by condition, and PMA by index by condition showed no significant interactions.

Control infants had a mean early-PMA STI of 83.61 (SD=7.87) and late-PMA STI of 73.16 (SD=7.62). This modest improvement (12.5%) in NNS STI over the 2.5 week study period may be attributed to maturation, as indicated by marginal significance for PMA at session $[F(1,26)=4.28, p=0.049]$ or to small sample size.

The decrease in spatiotemporal variability of non-nutritive suck following stimulation therapy demonstrates the potent effect of a synthetic orosensory pattern on ororhythmic development among preterm infants. Patterned oral cutaneous stimulation capitalizes on the responsiveness of the sCPG circuitry to peripheral inputs by providing infants who have poor oromotor skills with a controlled regimen of spatiotemporal cues to accelerate the development of suck.

An infant's ability to produce patterned oromotor output can predict their current health status as well as future outcomes. Non-nutritive suck has beneficial effects on the infant's behavioral state and reduces stress and restlessness. A functional NNS is also an important precursor to successful oral feeding, which is supported by the findings in the current report. The high levels of spatiotemporal instability in the suck pressure waveforms exhibited by the control infants was associated with only modest gains in percent oral feed (12% at early-PMA phase versus 36% at late-PMA phase). In contrast, STI values indicative of a highly organized suck. For these infants, the oral feed growth function was pronounced with a mean percent oral feed of only 4% at early-PMA phase (pre-stimulation) compared to 72% at late-PMA phase (post-stimulatuion). This finding demonstrates a strong positive relation between NNS proficiency and oral feed outcomes.

Timely transition to oral feeding is important for premature infants because it demonstrates motor system integrity and allows them to be discharged from the hospital. If not addressed early, poor feeding skills in infancy can continue to be problematic later on, as children who were preterm make up nearly half the population in feeding disorder clinics. Oromotor dyscoordination, however, is not isolated to feeding issues, but may serve as a powerful clinical marker for neurodevelopmental outcomes. For example, children with severe neurodevelopmental problems at 18 months tend to have arrhythmic nutritive expression/suction patterns as premature infants.

FIG. 22A shows the waveforms and NNS STI of a control group subject recorded during the initial assessment and the final assessment of the study. During the study, the control subject's NNS STI went from 89 to 81 indicating an improvement of NNS skill. FIG. 22B shows the waveforms and NNS STI of a stimulation group subject recorded during the initial assessment and the final assessment of the study. During the study, the subjects NNS STI went from 99 to 50 indicating substantial improvement of NNS skill compared to the control group subject. Plots of the selected bursts used to determine the NNS STI show substantial correlation at the conclusion of the study indicating the stimulation group subject had developed very coordinated NNS behavior.

This application is intended to cover adaptations and variations of the present subject matter. It is to be understood that the above description is intended to be illustrative, and not restrictive. The scope of the present subject matter should be determined with reference to the appended claims, along with the full scope of legal equivalents to which the claims are entitled.

What is claimed is:

1. An apparatus, comprising:
a non-nutritive pacifier;
a pressure transducer in communication with the pacifier to sense pressure applied to the pacifier;
a spatiotemporal index (STI) generator configured to generate a plurality of digitized, non-nutritive suck (NNS) pressure samples using the non-nutritive pacifier and the pressure transducer, to determine a plurality of standard deviations of a plurality of burst data sets using the plurality of digitized NNS pressure samples, wherein each standard deviation is based on a burst data point value associated with a particular sample of each of a plurality of normalized burst data sets, and to sum the plurality of standard deviations to provide a spatiotemporal index (STI) of non-nutritive suck pattern stability, wherein the STI is configured to provide a composite indication of variability of amplitude, and duration of a plurality of portions of the NNS pressure samples.

2. The apparatus of claim 1, wherein STI generator includes a peak selector, the peak selector configured to receive a minimum peak threshold and to identify peaks within a NNS pressure sample of the plurality of NNS pressure samples using the minimum peak threshold.

3. The apparatus of claim 2, wherein the STI generator includes a burst selector, the burst selector configured receive peak identification information from the peak selector and to identify the plurality of burst data sets using the peak identification information.

4. The apparatus of claim 3, wherein the peak identification information can include shoulder peak information and the burst selector is configured to delete at least a portion of the shoulder peak information to identify the plurality of burst data sets.

5. The apparatus of claim 3, wherein the STI generator includes a burst queue configured to store the plurality of burst data sets.

6. The apparatus of claim 5, wherein the STI generator is configured to normalize the plurality of burst data sets to generate the plurality of normalized burst data sets.

7. The apparatus of claim 6, wherein the normalized burst data sets include time normalized data points of the burst data sets and amplitude normalized data points of the burst data sets.

8. The apparatus of claim 6 wherein the STI generator includes a STI waveform generator configured to receive the plurality of normalized burst data sets and to determine the plurality of standard deviations.

9. The apparatus of claim 8, wherein the STI generator includes a NNS-STI processor is configured to receive the plurality of standard deviations, and to sum the plurality of standard deviations to provide a spatiotemporal index (STI) of non-nutritive suck pattern stability.

10. The apparatus of claim 1, including a display coupled to the STI generator to display the STI.

11. An apparatus, comprising:
a non-nutritive pacifier;
a pressure transducer in communication with the pacifier to sense pressure applied to the pacifier;
a processor configured to receive pressure information from the pressure transducer and to generate a plurality of digitized, non-nutritive suck (NNS) pressure samples using the pressure information, to determine a plurality of standard deviations of a plurality of burst data sets, wherein each standard deviation is based on a burst data point value associated with a particular sample of each of a plurality of normalized burst data sets, and to sum the plurality of standard deviations to provide a spatiotemporal index (STI) of non-nutritive suck pattern stability, wherein the STI is configured to provide a composite indication of variability of amplitude, and duration of a plurality of portions of the NNS pressure samples.

12. The apparatus of claim 11, wherein the processor is configured to detect at least a predetermined number of sequential pressure peaks in each of the plurality of burst data sets.

13. The apparatus of claim 12, wherein the processor is configured to generate the plurality of normalized burst data sets from the plurality of digitized NNS pressure samples.

14. The apparatus of claim 11, including a display coupled to the processor to display the STI.

\* \* \* \* \*